United States Patent
Blair

(10) Patent No.: US 9,717,565 B2
(45) Date of Patent: Aug. 1, 2017

(54) WIRELESSLY DETECTABLE OBJECTS FOR USE IN MEDICAL PROCEDURES AND METHODS OF MAKING SAME

(71) Applicant: COVIDIEN LP, Mansfield, MA (US)

(72) Inventor: William A. Blair, San Diego, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/003,515

(22) Filed: Jan. 21, 2016

(65) Prior Publication Data

US 2016/0206399 A1 Jul. 21, 2016

Related U.S. Application Data

(60) Provisional application No. 62/106,052, filed on Jan. 21, 2015.

(51) Int. Cl.
*A61B 90/98* (2016.01)
*G06K 7/10* (2006.01)
(Continued)

(52) U.S. Cl.
CPC ............... *A61B 90/98* (2016.02); *A61B 34/20* (2016.02); *G06K 7/10366* (2013.01);
(Continued)

(58) Field of Classification Search
CPC ............ A61B 2562/08; A61B 5/04085; A61B 5/04286; A61B 5/14532; A61B 90/98; A61B 19/0248; A61B 2050/105
(Continued)

(56) References Cited

U.S. PATENT DOCUMENTS 2,740,405 A   4/1956   Riordan
3,422,816 A   1/1969   Robinson et al.
(Continued)

FOREIGN PATENT DOCUMENTS

AU   2003249257 A1   2/2004
CN   101460096 A     6/2009
(Continued)

OTHER PUBLICATIONS

Black, "Method and Apparatus to Account for Transponder Tagged Objects During Clinical Procedures, Employing a Trocar," U.S. Appl. No. 62/360,869, filed Jul. 11, 2016, 99 pages.
(Continued)

*Primary Examiner* — Mark Blouin

(57) ABSTRACT

Various embodiments of a wirelessly detectable object to be used in medical procedures are provided. One example wirelessly detectable object includes a radio frequency identification (RFID) transponder that, when interrogated, wirelessly returns a first response signal that contains identification information associated with a surgical object. The wirelessly detectable object further includes a presence transponder that, when interrogated, wirelessly returns a second response signal that does not contain identification information. The presence transponder is received and freely movable within a pouch. The presence transponder is independently movable with respect to the RFID transponder. Another example wirelessly detectable object includes at least one active antenna element and at least one passive antenna element that together operate as a directional antenna.

34 Claims, 9 Drawing Sheets

(51) Int. Cl.
*A61B 34/20* (2016.01)
*A61B 50/37* (2016.01)
*A61B 90/90* (2016.01)

(52) U.S. Cl.
CPC .............. *A61B 50/37* (2016.02); *A61B 90/90* (2016.02); *A61B 2034/2051* (2016.02)

(58) Field of Classification Search
USPC ...................................................... 340/572.1
See application file for complete search history.

(56) References Cited

U.S. PATENT DOCUMENTS

| | | |
|---|---|---|
| 4,114,601 A | 9/1978 | Abels |
| 4,193,405 A | 3/1980 | Abels |
| 4,477,256 A | 10/1984 | Hirsch |
| 4,626,251 A | 12/1986 | Shen |
| 4,681,111 A | 7/1987 | Silvian |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,992,675 A | 2/1991 | Conner, Jr. et al. |
| 5,049,219 A | 9/1991 | Johns et al. |
| 5,057,095 A | 10/1991 | Fabian |
| 5,090,410 A | 2/1992 | Saper et al. |
| 5,105,829 A | 4/1992 | Fabian et al. |
| 5,107,862 A | 4/1992 | Fabian et al. |
| 5,112,325 A | 5/1992 | Zachry |
| 5,188,126 A | 2/1993 | Fabian et al. |
| 5,190,059 A | 3/1993 | Fabian et al. |
| 5,224,593 A | 7/1993 | Bennett |
| 5,231,273 A | 7/1993 | Caswell et al. |
| 5,235,326 A | 8/1993 | Beigel et al. |
| 5,329,944 A | 7/1994 | Fabian et al. |
| D353,343 S | 12/1994 | Eberhardt |
| 5,446,447 A | 8/1995 | Carney et al. |
| 5,456,718 A | 10/1995 | Szymaitis |
| 5,650,596 A | 7/1997 | Morris et al. |
| 5,664,582 A | 9/1997 | Szymaitis |
| 5,923,001 A | 7/1999 | Morris et al. |
| 5,931,824 A | 8/1999 | Stewart et al. |
| 5,963,132 A | 10/1999 | Yoakum |
| 6,026,818 A | 2/2000 | Blair et al. |
| 6,093,869 A | 7/2000 | Roe et al. |
| 6,201,469 B1 | 3/2001 | Balch et al. |
| 6,211,666 B1 | 4/2001 | Acker |
| 6,232,878 B1 | 5/2001 | Rubin |
| 6,276,033 B1 | 8/2001 | Johnson et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| 6,384,296 B1 | 5/2002 | Roe et al. |
| 6,401,722 B1 | 6/2002 | Krag |
| 6,441,741 B1 | 8/2002 | Yoakum |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,641,039 B2 | 11/2003 | Southard |
| 6,648,223 B2 | 11/2003 | Boukhny et al. |
| 6,650,143 B1 | 11/2003 | Peng |
| 6,650,240 B2 | 11/2003 | Lee et al. |
| 6,667,902 B2 | 12/2003 | Peng |
| 6,671,040 B2 | 12/2003 | Fong et al. |
| 6,696,954 B2 | 2/2004 | Chung |
| 6,700,151 B2 | 3/2004 | Peng |
| 6,734,795 B2 | 5/2004 | Price |
| 6,753,783 B2 | 6/2004 | Friedman et al. |
| 6,766,960 B2 | 7/2004 | Peng |
| 6,774,800 B2 | 8/2004 | Friedman et al. |
| 6,777,623 B2 | 8/2004 | Ballard |
| 6,777,757 B2 | 8/2004 | Peng et al. |
| 6,778,089 B2 | 8/2004 | Yoakum |
| 6,786,405 B2 | 9/2004 | Wiedenhoefer |
| 6,791,891 B1 | 9/2004 | Peng et al. |
| 6,798,693 B2 | 9/2004 | Peng |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,822,888 B2 | 11/2004 | Peng |
| 6,838,990 B2 | 1/2005 | Dimmer |
| 6,856,540 B2 | 2/2005 | Peng et al. |
| D502,419 S | 3/2005 | Copen |
| 6,861,639 B2 | 3/2005 | Al-Ali |
| 6,861,954 B2 | 3/2005 | Levin |
| 6,875,199 B2 | 4/2005 | Altman |
| 6,879,300 B2 | 4/2005 | Rochelle et al. |
| 6,898,116 B2 | 5/2005 | Peng |
| 6,909,366 B1 | 6/2005 | Marsh et al. |
| 6,940,751 B2 | 9/2005 | Peng et al. |
| 6,956,258 B2 | 10/2005 | Peng |
| 6,972,986 B2 | 12/2005 | Peng et al. |
| 6,977,504 B2 | 12/2005 | Wright et al. |
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,031,209 B2 | 4/2006 | Wang et al. |
| 7,042,722 B2 | 5/2006 | Suzuki et al. |
| D526,586 S | 8/2006 | McCaghren et al. |
| 7,098,793 B2 | 8/2006 | Chung |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| 7,307,530 B2 | 12/2007 | Fabian et al. |
| 7,319,396 B2 | 1/2008 | Homanfar et al. |
| 7,319,397 B2 | 1/2008 | Chung et al. |
| 7,325,723 B2 | 2/2008 | Desjeux |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,420,468 B2 | 9/2008 | Fabian et al. |
| 7,423,535 B2 | 9/2008 | Chung et al. |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| 7,513,425 B2 | 4/2009 | Chung |
| 7,557,710 B2 | 7/2009 | Sanchez et al. |
| 7,596,850 B2 | 10/2009 | Barth et al. |
| 7,609,538 B1 | 10/2009 | Lee et al. |
| 7,644,016 B2 | 1/2010 | Nycz et al. |
| 7,696,877 B2 | 4/2010 | Barnes et al. |
| 7,703,674 B2 | 4/2010 | Stewart et al. |
| 7,769,422 B2 | 8/2010 | DiSilvestro et al. |
| 7,795,491 B2 | 9/2010 | Stewart et al. |

(56) References Cited

U.S. PATENT DOCUMENTS

| | | |
|---|---|---|
| 7,837,694 B2 | 11/2010 | Tethrake et al. |
| 7,855,656 B2 | 12/2010 | Maschke |
| 7,876,097 B2 | 1/2011 | Greim |
| 7,898,420 B2 | 3/2011 | Blair et al. |
| 8,082,192 B2 | 12/2011 | Nycz et al. |
| 8,105,296 B2 | 1/2012 | Morris et al. |
| 8,181,860 B2 * | 5/2012 | Fleck .................... A61G 13/10 235/380 |
| 8,193,938 B2 | 6/2012 | Halberthal et al. |
| 8,256,674 B2 | 9/2012 | Fleck et al. |
| 8,259,518 B2 | 9/2012 | Peng et al. |
| 8,279,068 B2 | 10/2012 | Morris et al. |
| 8,358,212 B2 | 1/2013 | Blair |
| 8,454,613 B2 | 6/2013 | Tethrake et al. |
| 8,477,076 B1 | 7/2013 | Nero, Jr. et al. |
| 8,479,989 B2 | 7/2013 | Fleck et al. |
| 8,576,076 B2 | 11/2013 | Morris et al. |
| 8,624,721 B2 | 1/2014 | Barker, Jr. et al. |
| 8,710,957 B2 | 4/2014 | Blair et al. |
| 8,726,911 B2 | 5/2014 | Blair |
| 8,780,660 B2 | 7/2014 | Peng |
| 8,872,662 B2 | 10/2014 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,168,104 B2 | 10/2015 | Dein |
| 9,414,973 B2 | 8/2016 | Fleck et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2004/0008123 A1 | 1/2004 | Carrender et al. |
| 2004/0137844 A1 | 7/2004 | Desjeux et al. |
| 2004/0250819 A1 | 12/2004 | Blair et al. |
| 2005/0049564 A1 | 3/2005 | Fabian |
| 2005/0110640 A1 | 5/2005 | Chung |
| 2005/0131397 A1 | 6/2005 | Levin |
| 2005/0203470 A1 * | 9/2005 | Ballard .................. G01G 17/00 604/362 |
| 2005/0212673 A1 | 9/2005 | Forster |
| 2005/0249036 A1 | 11/2005 | Davies et al. |
| 2005/0267550 A1 | 12/2005 | Hess et al. |
| 2006/0054107 A1 | 3/2006 | Baker |
| 2006/0084934 A1 | 4/2006 | Frank |
| 2006/0106368 A1 | 5/2006 | Miller et al. |
| 2006/0187044 A1 | 8/2006 | Fabian et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0270933 A1 | 11/2006 | Benson et al. |
| 2007/0051473 A1 | 3/2007 | Speich |
| 2007/0069866 A1 | 3/2007 | Schuessler et al. |
| 2007/0109099 A1 | 5/2007 | Raphaeli et al. |
| 2007/0125392 A1 | 6/2007 | Olson, Jr. et al. |
| 2007/0152823 A1 | 7/2007 | Hirahara et al. |
| 2007/0209957 A1 | 9/2007 | Glenn et al. |
| 2007/0216062 A1 | 9/2007 | Frank |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0265690 A1 | 11/2007 | Lichtenstein et al. |
| 2007/0270660 A1 | 11/2007 | Caylor, III et al. |
| 2008/0001760 A1 | 1/2008 | Oh et al. |
| 2008/0007411 A1 | 1/2008 | Levin |
| 2008/0020189 A1 | 1/2008 | Hofmair et al. |
| 2008/0024277 A1 * | 1/2008 | Volpi .................... G01S 13/66 340/10.1 |
| 2008/0051746 A1 | 2/2008 | Shen-Gunther |
| 2008/0086771 A1 | 4/2008 | Li et al. |
| 2008/0132860 A1 | 6/2008 | Smith et al. |
| 2008/0231452 A1 | 9/2008 | Levin |
| 2008/0281190 A1 | 11/2008 | Petcavich et al. |
| 2008/0296373 A1 | 12/2008 | Zmood et al. |
| 2009/0051485 A1 | 2/2009 | Corry et al. |
| 2009/0267765 A1 | 10/2009 | Greene et al. |
| 2009/0322485 A1 | 12/2009 | Barnes et al. |
| 2010/0033309 A1 | 2/2010 | Blair |
| 2010/0109848 A1 | 5/2010 | Blair et al. |
| 2011/0181394 A1 | 7/2011 | Blair |
| 2011/0277359 A1 | 11/2011 | Halberthal et al. |
| 2012/0031547 A1 | 2/2012 | Halberthal et al. |
| 2013/0199720 A1 | 8/2013 | Halberthal et al. |
| 2014/0068915 A1 | 3/2014 | Halberthal et al. |
| 2014/0243770 A1 | 8/2014 | Stewart |
| 2014/0303580 A1 | 10/2014 | Blair |
| 2015/0054625 A1 | 2/2015 | Blair et al. |
| 2015/0164603 A1 | 6/2015 | Fleck et al. |
| 2015/0216610 A1 | 8/2015 | Augustine |
| 2015/0272688 A1 | 10/2015 | Blair et al. |
| 2015/0317555 A1 | 11/2015 | Dor et al. |
| 2016/0157957 A1 | 6/2016 | Blair |
| 2016/0206399 A1 | 7/2016 | Blair |
| 2016/0210548 A1 | 7/2016 | Blair |
| 2016/0250000 A1 | 9/2016 | Blair |
| 2016/0259954 A1 | 9/2016 | Buhler et al. |

FOREIGN PATENT DOCUMENTS

| | | |
|---|---|---|
| EP | 1 612 554 A1 | 1/2006 |
| EP | 2 087 850 A2 | 8/2009 |
| JP | 2009539478 A | 11/2009 |
| WO | 86/02539 A1 | 5/1986 |
| WO | 02/39917 A1 | 5/2002 |
| WO | 03/073934 A1 | 9/2003 |
| WO | 2004/008387 A1 | 1/2004 |
| WO | 2004/054801 A1 | 7/2004 |
| WO | 2004/086997 A1 | 10/2004 |
| WO | 2006/060781 A1 | 6/2006 |
| WO | 2007/120736 A2 | 10/2007 |
| WO | 2007/146091 A1 | 12/2007 |
| WO | 2008/008449 A2 | 1/2008 |
| WO | 2008/024921 A1 | 2/2008 |
| WO | 2008/106552 A1 | 9/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |

OTHER PUBLICATIONS

Black, "Method and Apparatus to Account for Transponder Tagged Objects Used During Clinical Procedures, Employing a Trocar," U.S. Appl. No. 62/378,515, filed Aug. 23, 2016, 103 pages.

Hansen et al., "Method and Apparatus to Account for Transponder Tagged Objects Used During Clinical Procedures, Employing a Shielded Receptacle," U.S. Appl. No. 62/360,864, filed Jul. 11, 2016, 99 pages.

Hansen et al., "Method and Apparatus to Account for Transponder Tagged Objects Used During Clinical Procedures Employing a Shielded Receptacle With Antenna," U.S. Appl. No. 62/360,866, filed Jul. 11, 2016, 154 pages.

Poirier et al., "Method and Apparatus to Account for Transponder Tagged Objects Used During Clinical Procedures, for Example Including Count in and/or Count Out and Presence Detection," U.S. Appl. No. 62/360,868, filed Jul. 11, 2016, 113 pages.

Poirier et al., "Method and Apparatus to Account for Transponder Tagged Objects Used During Clinical Procedures, for Example Including Count in and/or Count Out and Presence Detection," U.S. Appl. No. 62/378,511, filed Aug. 23, 2016, 114 pages.

Barnes et al., "Method, Apparatus and Article for Detection of Transponder Tagged Objects, for Example During Surgery," U.S. Appl. No. 61/056,787, filed May 28, 2008, 60 pages.

(56) References Cited

OTHER PUBLICATIONS

Barnes et al., "Method, Apparatus and Article for Detection of Transponder Tagged Objects, for Example During Surgery," U.S. Appl. No. 61/091,667, filed Aug. 25, 2008, 76 pages.

Blair et al., "Improved Apparatus and Method for Detecting Objects Using Tags and Wideband Detection Device," U.S. Appl. No. 60/811,376, filed Jun. 6, 2006, 16 pages.

Blair et al., "Method and Apparatus to Detect Transponder Tagged Objects, for Example During Surgery," U.S. Appl. No. 61/109,104, filed Oct. 28, 2008, 73 pages.

Blair et al., "Method and Apparatus to Detect Transponder Tagged Objects, for Example During Surgery," U.S. Appl. No. 61/222,443, filed Jul. 1, 2009, 95 pages.

Blair et al., "Method and Apparatus to Detect Transponder Tagged Objects, for Example During Medical Procedures," U.S. Appl. No. 61/242,704, filed Sep. 15, 2009, 127 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Tag and Detection Device," U.S. Appl. No. 60/458,222, filed Mar. 27, 2003, 23 pages.

Blair et al., "Transponder Housing and Device to Mark Implements, Such as Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Blair, "Article to Attach a Transponder to a Surgical Sponge," Design U.S. Appl. No. 29/336,009, filed Apr. 27, 2009, 4 pages.

Blair, "Attachment Article to Attach a Transponder to a Surgical Sponge," Design U.S. Appl. No. 29/336,007, filed Apr. 27, 2009, 4 pages.

Blair, "Attachment Article to Attach a Transponder to a Surgical Sponge," Design U.S. Appl. No. 29/336,008, filed Apr. 27, 2009, 7 pages.

Blair, "Detectable Surgical Objects and Methods of Making Same," U.S. Appl. No. 61/109,142, filed Oct. 28, 2008, 47 pages.

Blair, "Method and Apparatus to Account for Transponder Tagged Objects Used During Medical Procedures," U.S. Appl. No. 61/263,726, filed Nov. 23, 2009, 78 pages.

Blair, "Multi-Modal Transponder and Method and Apparatus to Detect Same," U.S. Appl. No. 61/102,749, filed Oct. 3, 2008, 48 pages.

Blair, "Radio Opaque Device With Resonant Nanostructures," U.S. Appl. No. 61/163,813, filed Mar. 26, 2009, 47 pages.

Blair, "Transponder Device to Mark Implements, Such as Surgical Implements, and Method of Manufacturing and Using Same," U.S. Appl. No. 61/086,727, filed Aug. 6, 2008, 30 pages.

Blair, "Transponder Device to Mark Implements, Such as Surgical Implements, and Method of Manufacturing and Using Same," U.S. Appl. No. 61/220,452, filed Jun. 25, 2009, 46 pages.

Blair, "Transponder Housing," Design U.S. Appl. No. 29/322,539, filed Aug. 6, 2008, 6 pages.

Blair, "Wirelessly Detectable Objects for Use in Medical Procedures and Methods of Making Same," U.S. Appl. No. 62/106,052, filed Jan. 21, 2015, 49 pages.

Blair, "Wirelessly Detectable Objects for Use in Medical Procedures and Methods of Making Same," U.S. Appl. No. 62/138,248, filed Mar. 25, 2015, 67 pages.

Blair, "Wirelessly Detectable Objects for Use in Medical Procedures and Methods of Making Same," U.S. Appl. No. 15/003,524, filed Jan. 21, 2016, 59 pages.

Clearcount Medical Solutions, "The SmartSponge System," Downloaded from http://clearcount.com on Oct. 20, 2009, 7 pages.

Haldor Advance Technologies, "Haldor Advanced Technologies Releases a Breakthrough New Sponge Management Solution: Modular, Mobile, Wireless, and Tailored per Use-case and Requirements," Sep. 8, 2015, retrieved from http://wwl.prweb.com/prfiles/2015/09/06/12938762/ORLocate%205Sponge%20Solution-September%202015.pdf, 2 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

European Search Report dated Jun. 24, 2016, for corresponding EP Application No. 16151391.6-1659, 8 pages.

* cited by examiner

WIRELESSLY DETECTABLE OBJECTS FOR USE IN MEDICAL PROCEDURES AND METHODS OF MAKING SAME

BACKGROUND

Technical Field

The present disclosure generally relates to detection of presence, or absence, and identification of objects tagged with wirelessly detectable objects, which may, for example, allow detection and identification of surgical objects (e.g., sponges, instruments, etc.) during or after surgery, or for inventorying of objects, for instance surgical objects.

Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or require multiple counts to be performed to track the use and return of objects during surgery. Such manual approaches are inefficient, requiring the time of highly trained personnel, and are prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

However, some of these approaches do not allow identification of the object. Conventional approaches that allow identification of the object via transmitting an identifier typically transmit a signal at frequencies that have a short range of detection, which may inhibit detection of the transponder, and thus, the object attached thereto. Furthermore, these transponders may not be detectable by the interrogation device when they are situated such that there is an obstacle or membrane, such skin or flesh, between the transponder and the interrogation device.

Consequently, a new approach to uniquely identify and detect presence and absence of a transponder assembly as well as identification is desirable.

BRIEF SUMMARY

It may be useful for a medical provider to be able to detect a transponder at longer ranges while still being able to receive an identifier from the transponder to uniquely identify the object. For example, upon detecting that an object is present in a proximity of the surgical site, particularly inside the body of the patient, it may be useful to wirelessly determine an identity of the object. Further, upon completion of surgery, it may useful to scan the objects that were used during surgery and are currently present, to identify them and determine whether all of the objects that were present before surgery are present after surgery outside the patient's body without requiring a manual count of the objects by highly trained and highly compensated personnel.

Additionally, identification of the object can also be useful in counting a number of packaged objects at completion of a manufacturing process to ensure that an appropriate number of objects are included in a shipping tote or other package. Identification of the object may also be useful in determining use history of an object, or the duration of time lapsed from a reference point in time relating to the object, such as a last maintenance time of the object. For example, in the medical or surgical context, tools such as those listed above, can have a limited shelf life after being disinfected and before being used or reused. Furthermore, some tools have a total life cycle after which they need to be replaced or go through maintenance before being reused. Conventional manual tracking of an object's life cycle, maintenance cycle, shelf life or any other parameter, even when assisted by computers, can be costly and time-consuming.

A wirelessly detectable object to use in medical procedures may be summarized as including: a radio frequency identification (RFID) transponder that wirelessly receives a first interrogation signal and wirelessly returns a first response signal that contains identification information associated with the wirelessly detectable object; a presence transponder that wirelessly receives a second interrogation signal and wirelessly returns a second response signal that does not contain identification information; a piece of absorbent material; and a pouch comprising at least a first flexible layer that forms an interior cavity, the presence transponder received and freely movable within the interior cavity, the presence transponder independently movable with respect to the RFID transponder, the pouch physically coupled to at least a portion of the piece of absorbent material.

The presence transponder may be not directly physically attached to the RFID transponder. The RFID transponder may be received within the interior cavity. The RFID transponder may be received and freely movable within the interior cavity. The RFID transponder may form at least a portion of the first flexible layer, may be embedded within the first flexible layer, or may be adhered to the first flexible layer. The RFID transponder may include an RFID chip and an antenna trace. Either or both of the RFID chip and the antenna trace may be embedded within the first flexible layer. The antenna trace of the RFID transponder may include an active antenna element, the wirelessly detectable object may further include a passive antenna element, and the active antenna element and the passive antenna element together may form a directional antenna. The passive antenna element may be embedded in the first flexible layer. The first flexible layer may be physically coupled to the piece of absorbent material to form the interior cavity therebetween and at least the active antenna element of the RFID transponder may be received within the interior cavity and adhered to the piece of absorbent material. The pouch may further include a second flexible layer physically coupled to the first flexible layer to form the interior cavity therebetween, the second flexible layer different than the piece of absorbent material. The RFID transponder may form at least a portion of the second flexible layer, may be embedded within the second flexible layer, or may be adhered to the second flexible layer. The wirelessly detectable object may further include: a passive antenna element embedded in or adhered to the first flexible layer, the passive antenna element and the RFID transponder together forming a directional antenna. The pouch may further include a radio frequency (RF) weld that extends around a perimeter of the interior cavity, may physically couple the first flexible layer to the second flexible layer, and may seal the presence transponder within the interior cavity. The RF weld may include a first RF weld and wherein the first RF weld or a second RF weld may further physically couple the pouch to the piece of absorbent material. One or both of the first flexible layer and second flexible layer may be a fabric laminate. The pouch may further include a radio frequency (RF) weld that extends around a perimeter of the interior cavity, may physically couple the first flexible layer to the piece of absorbent material, and may seal the presence transponder within the interior cavity. The first flexible layer may be formed of a fabric laminate. The fabric laminate may include thermoplastic polyurethane and nylon fabric or polyvinyl chloride (PVC) impregnated fabric.

A wirelessly detectable object to use in medical procedures may be summarized as including: a piece of absorbent material; a first substrate physically coupled to the piece of absorbent material; a radio frequency identification (RFID) transponder to wirelessly receive a first interrogation signal and wirelessly return a first response signal that contains identification information associated with the wirelessly detectable object, the RFID transponder comprising an active antenna element; and a passive antenna element; wherein the passive antenna element and the active antenna element together operate as a directional antenna and the first substrate carries at least one of the active antenna element and the passive antenna element.

The first substrate may include a layer of fabric laminate. The fabric laminate may be physically coupled to the piece of absorbent material to form an interior cavity therebetween and the wirelessly detectable object may further include a presence transponder received and freely movable within the interior cavity, the presence transponder to wirelessly return a second response signal that does not contain identification information. The RFID transponder may be embedded in or adhered to the layer of fabric laminate or may be received within the interior cavity and adhered to the piece of absorbent material. The passive antenna element may be located between the piece of absorbent material and the layer of fabric laminate and the active antenna element may be embedded in, adhered to, or forms a portion of the layer of fabric laminate. The active antenna element may be located between the piece of absorbent material and the layer of fabric laminate and the passive antenna element may be embedded in, adhered to, or forms a portion of the layer of fabric laminate. The layer of fabric laminate may be carried at least in part by one or more of the passive antenna element and the active antenna element. The wirelessly detectable object may further include: a second layer of fabric laminate located between the passive antenna element and the piece of absorbent material. The wirelessly detectable object may further include: a presence transponder physically coupled to the piece of absorbent material, the presence transponder to wirelessly return a second response signal that does not contain identification information. The directional antenna may include a Yagi antenna. One or both of the active antenna element and the passive antenna element may include conductive traces embedded within or carried on the first substrate.

A method to account for surgical objects used in medical procedures may be summarized as including: providing a plurality of surgical objects that have a plurality of wirelessly detectable objects respectively physically coupled thereto, each wirelessly detectable object comprising a radio frequency identification (RFID) transponder and a presence transponder; interrogating the RFID transponder of each surgical object introduced into a surgical field; receiving, from the interrogated RFID transponder of each surgical object introduced into the surgical field, a first response signal that contains identification information stored by such RFID transponder; generating a first manifest of surgical objects introduced into the surgical field based at least in part on the identification information included in each first response signal; prior to completion of a medical procedure, scanning the surgical field to interrogate any presence transponders that remain within the surgical field; determining whether any surgical objects remain within the surgical field based at least in part on whether one or more second response signals are respectively received from one or more presence transponders responsive to the scanning, wherein the one or more second response signals do not contain identification information; interrogating the RFID transponder of each surgical object removed from the surgical field; receiving, from the interrogated RFID transponder of each surgical object removed from the surgical field, a third response signal that contains the identification information stored by such RFID transponder; and generating a second manifest of surgical objects removed from the surgical field based at least in part on the identification information included in each third response signal.

Receiving a first response signal may include receiving the first response signal that is within a first frequency range. Determining whether any surgical objects remain within the surgical field may include determining whether any surgical objects remain within the surgical field based at least in part on whether one or more second response signals are respectively received from one or more presence transponders responsive to the scanning, the one or more second response signals within a second frequency range that provides superior transmission through bodily tissue relative to the first frequency range. Receiving a first response signal may include receiving the first response signal at a first physical distance from each RFID transponder. Determining whether any surgical objects remain within the surgical field may include determining whether any surgical objects remain within the surgical field based at least in part on whether one or more second response signals are respectively received at a second physical distance from one or more presence transponders responsive to the scanning, the second physical distance greater than the first physical distance. The method to account for surgical objects may further include comparing the first manifest to the second manifest to determine whether one or more surgical objects remain within the surgical field.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers, and types of objects employed in medical procedures, for instance sponges, gauze or other absorbent objects, have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a surgical environment will be used as an example environment for detecting objects but such should not be considered limiting.

Figure 1A:
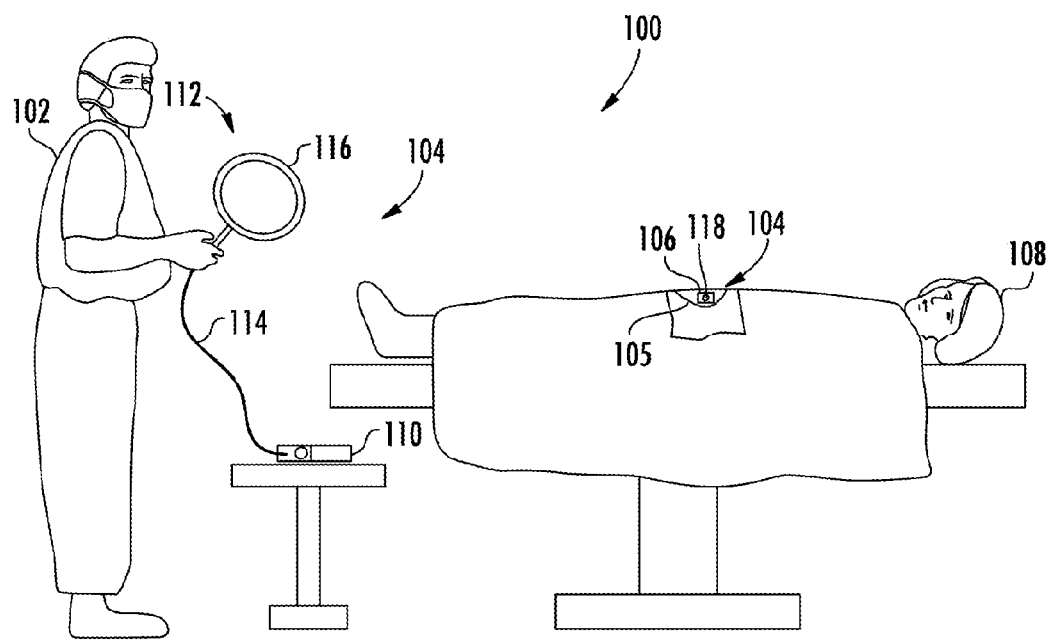
FIG. 1A is a schematic diagram illustrating a surgical environment where a medical provider uses an interrogation and detection system to detect an object tagged with a wirelessly detectable object in a patient, according to one illustrated embodiment.

FIG. 1A shows a surgical environment 100 in which medical procedures are performed, for example a surgical environment, clinician's office, examination room, patient room or other environments in which medical procedures may be performed. A medical provider 102 operates an identification and detection system 104 to ascertain the presence or absence of objects 106 in, or on, a patient 108, for example in or on a surgical site or area or cavity 105, and/or an identity of such objects 106.

The object 106 may take a variety of forms, for example instruments, accessories and/or disposable objects useful in performing surgical procedures. For instance, the object 106 may take the form of scalpels, scissors, forceps, hemostats, dilators, needles, a drill bit, and/or clamps or other surgically useful objects. Also for example, the objects 106 may take the form of surgical sponges, gauze and/or padding. The surgical sponges, gauze and/or padding may be, as examples, 2 inches by 2 inches, 4 inches by 4 inches, 12 inches by 12 inches, or other sizes. Such dimensions may refer to the surgical sponges, gauze and/or padding as folded or otherwise packaged.

According to an aspect of the present disclosure, the object 106 is tagged, carrying, attached or otherwise coupled to a wirelessly detectable object 118.

In particular, referring now to FIG. 1 B, a wirelessly detectable object 118 is physically coupled to or otherwise physically associated with each object 106 used within the surgical environment 100. The wirelessly detectable object 118 includes one or more transponders that receive and respond to wireless signals. For example, in some implementations, the wirelessly detectable object 118 includes a radio frequency identification (RFID) transponder 120 that, when interrogated, wirelessly returns a first response signal that contains identification information associated with the wirelessly detectable object 118. Alternatively or additionally, the wirelessly detectable object 118 includes a presence transponder 122 that, when interrogated, wirelessly returns a second response signal that does not contain identification information.

Thus, in some implementations, the medical provider 102 can operate the identification and detection system 104 to determine the presence or absence of wirelessly detectable object 118 through wireless interrogation of the presence transponder 122 and/or to obtain identification information through wireless interrogation of the RFID transponder 120. In particular, in some implementations, respective interrogation of and response by the presence transponder 122 and the RFID transponder 120 can occur in two different frequency ranges. For example, the frequency range associated with interrogation of and response by the presence transponder 122 can include lower frequencies than the frequency range associated with interrogation of and response by the RFID transponder 120. Such lower frequencies may enable superior transmission of signals through bodily tissues or other obstacles including membranes, skin, flesh, etc. Thus, in some implementations, interrogation of and response by the presence transponder 122 is possible at larger physical distances than interrogation of and response by the RFID transponder 120.

The RFID transponder 120 includes an integrated circuit electrically coupled to an antenna. The RFID transponder 120 may be relatively small, such as, for example, approximately 12 millimeters in diagonal.

In some implementations, the antenna can include an inductive winding such as a conductive wire wound about a core. The core can be fabricated from a ferrite rod. The inductive winding is electrically coupled to an integrated circuit. In other implementations, the antenna includes a conductive trace or other structures. The RFID transponder 120 may be an active device that includes a local power source such as a battery or may be a passive device that relies on energy in the interrogation signal to power the transponder 120. In one aspect, the RFID transponder 120 takes the form of any one of various commercially-available RFID devices that include an RFID integrated circuit and/or front end.

The RFID transponder 120 is operable to transmit (e.g., via active radiation of the antenna) a first response signal that contains identification information, in response to receiving an interrogation signal in a first frequency range. The first response signal encodes the identification information stored by the integrated circuit. As such, the RFID transponder 122 may be denominated as a "smart" transponder.

The identification information included in the first response signal may be a unique identifier (i.e., unique over a set of all otherwise identical RFID transponders 120). Alternatively, the identifier may not be unique, for example, a set of RFID transponders 120 may each have the same identifier. Even where the identifier is unique, some portion of the identification information or some other identification information may not be unique, for example, a portion representing a manufacturer, a lot, or a type, may be shared between transponders 120 from the same manufacturer, lot or of the same type. In some implementations, the identification information can be associated with a type of the object 106 or an attribute thereof. For example, the identification information can be linked to the type or attribute using a database, lookup table, or other data structure that cross-references unique identifiers with the type or attribute.

Alternatively, in implementations where the integrated circuit of the RFID transponder 120 has read and write capability, the identification information can include the desired attribute, pre-stored or written onto the integrated circuit, and directly convey the pre-stored attribute via the first response signal.

Furthermore, in some implementations, the RFID transponder 120 is a printable and/or ultra-low-cost RFID transponder 120 that is not necessarily intended to maintain functionality when the object 106 is used within the surgical environment 100. In particular, in such implementations, the RFID transponder 120 is interrogated at a conclusion of or during a manufacturing process, for example, to ensure that an appropriate number of objects 106 are included in a shipping tote or other package. After such use, the RFID transponder 120 may not be expected to provide further use and may allowably degrade or otherwise experience damage if the object 106 is used within the surgical environment 100 (e.g., in vivo). Such may permit inclusion of low-cost RFID transponders 120 for use in manufacturing without requiring a hardened or rugged encapsulant or transponder body to protect the transponders 120 during surgical procedures.

The presence transponder 122 may be constructed in various manners. For example, the presence transponder 122 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. For example, the inductive coil and capacitor may together form an inductive/capacitance (L/C) tank circuit. Additional details about types of transponders may be found in U.S. Provisional Patent Application Ser. No. 60/811,376 filed Jun. 6, 2006 and U.S. Provisional Patent Application Ser. No. 60/892,208, filed Feb. 28, 2007, both of which are incorporated herein by reference.

The presence transponder 122 is operable to transmit (e.g., via radiation of the inductive coil) a second response signal, in response to receiving an interrogation signal in a second frequency range. The second response signal does not include any unique identifying information and, therefore, indicates only that the presence transponder 122 is present. As such, the presence transponder 122 may be denominated as a "dumb" transponder. However, in some implementations, presence transponder 122 provides superior response strength through bodily tissue relative to the RFID transponder 120.

The presence transponder 122 may be relatively small, for example approximately 5-10 millimeters long with a diameter of about 1-4 millimeters. In at least some embodiments, an encapsulant advantageously protects the transponder from the ambient environment, for instance from forces, pressure and/or fluids, such as bodily fluids.

In some implementations, the presence transponder 122 includes a dumbbell-shaped ferrite rod having broad end portions and a narrow intermediate portion. The broad end portions may provide capacitive functionality. In other implementations, the presence transponder 122 may be shaped as a fusiform-shaped object, with truncated ends.

In further implementations, the wirelessly detectable object 118 includes at least one directional antenna. For example, in some implementations, an active antenna element of the RFID transponder 120 forms at least a portion of the directional antenna. In some implementations, the wirelessly detectable object does not include the presence transponder 122. Particular example structures and arrangements of the wirelessly detectable object 118 are discussed further below with reference to the Figures that follow.

Figure 1B:
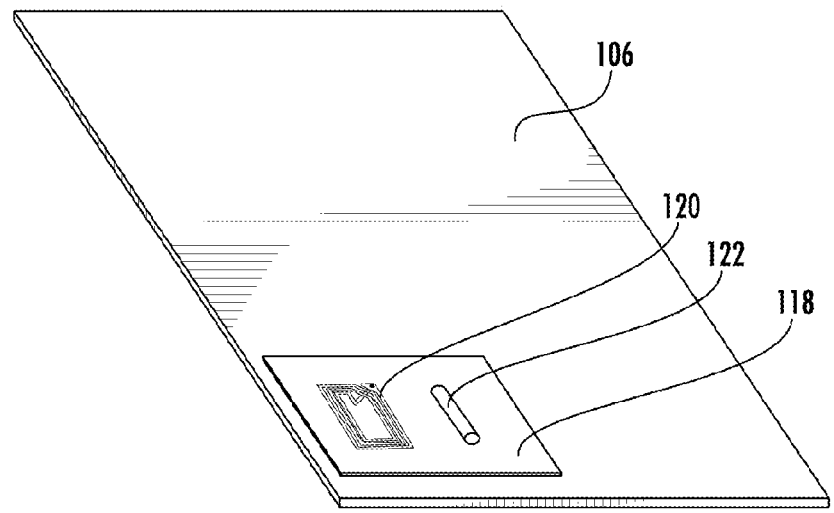
FIG. 1B is an isometric view of a surgical object tagged with a wirelessly detectable object, according to one illustrated embodiment.

Furthermore, although FIG. 1B depicts the wirelessly detectable object 118 as physically coupled to and visible upon an external surface of the object 106, such depiction is provided for ease of illustration and description only. In particular, in instances in which the object 106 is a piece of absorbent material such as surgical sponges, gauze, padding, or other absorbent materials, the piece of absorbent material 106 may be folded or otherwise manipulated such that the wirelessly detectable object 118 is no longer carried on an external surface of the piece of absorbent material 106 and/or externally visible. As an example, the piece of absorbent material 106 may be folded into quadrants to provide, for example, a folded sponge, gauze, or padding that has four discernable layers. As a result of the folding, the wirelessly detectable object 118 may be internally carried between layers of the piece of absorbent material 106 and visible only upon unfolding of the piece of absorbent material 106.

Referring again to FIG. 1A, the identification and detection system 104 includes a controller 110, and an interrogation device or assembly, such as an antenna 112 coupled to the controller 110 by one or more communication paths, for example a coaxial cable 114. The antenna 112 may take the form of a hand-held wand 116. In some implementations, the antenna 112 is sized to fit at least partially in the cavity 105.

The controller 110 is configured to cause the antenna 112 to emit one or more wireless interrogation signals in one or more frequency bands, to receive responses to such interrogation signals from one or more wirelessly detectable objects 118, and to determine the presence or absence and/or identity of the wirelessly detectable objects 118 or associated objects 106 based on the received response signals, if any.

In particular, the wand 116 can be configured to emit a first interrogation signal in a first frequency range and can include an integrated circuit tag reader, such as an RFID reader as is known, to receive the first response signal from the RFID transponder 120 and decode the identifier. The wand 116 can further be configured to emit a second interrogation signal in a second frequency, to receive the second response signal from the presence transponder 122, and to provide an indication of presence of the object 106 when the second response signal is received.

Specific details of components of the wand 116 are not discussed herein to not unnecessarily obscure the description of the embodiments. Components configured for emission of the interrogation signals and for receiving the first and second response signals can be selected from any suitable scanning technology, including, but not limited to, the detection device disclosed in U.S. Pat. No. 6,026,818, to Blair et al., and that disclosed in U.S. Pat. No. 7,696,877, to Barnes et al., both of which are incorporated herein by reference.

Furthermore, in some implementations, the controller 110 of the interrogation device or assembly includes an interface that displays the name of the objects 106 as the wand 116 scans the objects 106 after surgery. For example, the interface may display an accounting or inventory of sponges, gauzes, padding, hemostats, clamps, forceps, scissors, scalpels, or other surgical tools or accessories, or any other objects 106, for an expedient accounting of the objects 106.

As one example method of operation, a user, such as the medical provider 102, can scan the patient 108 to detect presence or absence of wirelessly detectable objects 118 and their corresponding objects 106 within the patient 108 through wireless interrogation of one or more presence transponders 122. For example, such interrogation of the presence transponders 122 can occur at a first physical distance. Upon detecting the presence of an object 106 within the patient 108, the medical provider 102 can immediately scan the region of detection to wirelessly interrogate one or more RFID transponders 120 and thereby identify the one or more objects 106 that remain. For example, such interrogation of the RFID transponders 120 can occur at a second physical distance that is less than the first physical distance. Having obtained the identity of the object 106, the medical provider 102 can make informed decisions with respect to handing of the object 106. For example, the medical provider 102 can remove object prior to closing patent.

As another example, upon removing the object or objects 106 from the body of the patient 108, and with all the present objects 106 laid out in an area after surgery and before closing the surgical site or area 105, the medical provider 102 can scan the present objects 106 to ensure that all the objects 106 that were present before surgery, are now present and outside of the body of the patient 108 after surgery. For example, the medical provider can interrogate the RFID transponder 120 of each wirelessly detectable object 118 to identify all present objects 106. The presently identified objects 106 can be compared to a list of objects 106 identified and logged prior to use within the surgical environment to detect any discrepancies (i.e., missing objects).

As yet another example method of operation, one or more RFID transponders 120 for one or more objects 106 may be interrogated at a conclusion of or during a manufacturing process, for example, to ensure that an appropriate number of objects 106 are included in a shipping tote or other package. Upon entry into and use of the objects 106 within the surgical environment, the RFID transponders 120 may or may not degrade. However, the medical provider 102 may still interrogate one or more presence transponders 122 to advantageously detect presence or absence of wirelessly detectable objects 118 and their corresponding objects 106 within the patient 108.

Accordingly, the wirelessly detectable objects 118 of the present disclosure provide the capability to efficiently detect objects 106 that may be present in or on the body of the patient 108, and the capability to conduct an inventory of present objects 106 after surgery to ensure all objects 106 used during surgery are present, without the use of multiple separately affixed optically-readable tags and without the need to conduct a manual count of the objects by highly trained and highly paid personnel.

Further, although a human patient 108 is illustrated, the described interrogation and detection system 104 may similarly be used on animals or inanimate subjects.

Figure 2A:
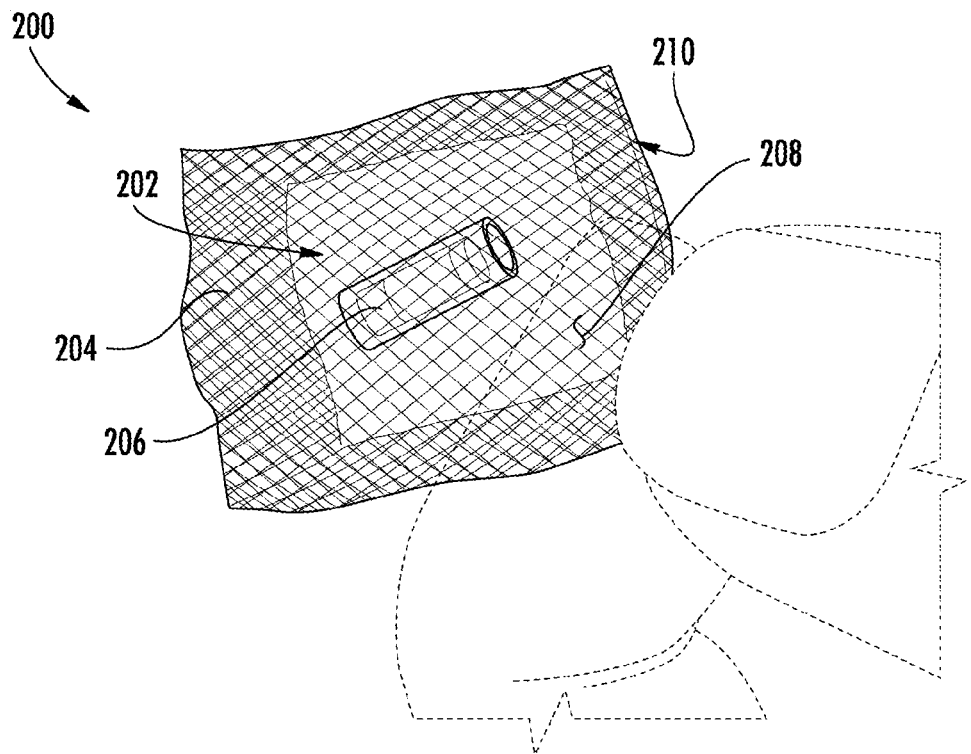
FIG. 2A is a front view of a pouch that includes a presence transponder, according to one illustrated embodiment.

FIG. 2A is a front view 200 of a pouch 202 that includes a presence transponder 206, according to one illustrated embodiment. In particular, in some implementations of the present disclosure, the wirelessly detectable object 118 includes a pouch 202 that holds or otherwise retains a presence transponder 206 within an interior cavity of the pouch 202. The pouch 202 is physically coupleable to an object 106 such as a piece of absorbent material.

In some implementations, the presence transponder 206 is freely movable within the interior cavity of the pouch 202. Such may advantageously allow folding, stretching, compression, twisting, or other physical manipulation of the piece of absorbent material or other object 106 without causing damage to the presence transponder 206. For example, the presence transponder 206 freely moves within the pouch 202 to an advantageous position experiencing reduced forces. Likewise, the free-floating presence transponder 206 does not inhibit folding, stretching, compression, twisting, or other physical manipulation of the piece of absorbent material or other object 106 which may be necessary for the surgical procedure.

The pouch 202 includes at least a first flexible layer 208 that forms the interior cavity. For example, the first flexible layer 208 can be physically coupled to a surface of an object 106 such as a piece of absorbent material to form the interior cavity therebetween. As another example, as shown in FIG. 2A, the pouch 202 includes a second flexible layer 210 opposite the first flexible layer 208 and physically coupled to the first flexible layer 208 to form the interior cavity therebetween.

In some implementations, a radio frequency (RF) weld 204 physically couples the first flexible layer 208 to the second flexible layer 210. For example, the RF weld 204 extends around a perimeter of the interior cavity and seals the presence transponder 206 within the pouch 202. A width of the RF weld 204 can be varied to balance various objectives such as a strength of weld 204 and a size of the pouch 202. Alternatively or additionally to RF weld 204, adhesives, stitching, clamping, fasteners, or other securing means can physically couple the first flexible layer 208 to the object 106 or the second flexible layer 210.

The first and/or second flexible layers 208 and 210 may be fabric laminates or other materials. For example, the first and/or second flexible layers 208 and 210 may be one or more of thermoplastic polyurethane (TPU) and nylon fabric; polyvinyl chloride (PVC) impregnated fabric; layer(s) of PVC, TPU, PET, PETG, LDPE, EVA, open celled polyurethanes, or nylon; other fabrics (e.g., cotton); other plastics; or combinations thereof. The flexible layers 208 and 210 are typically relatively thin and may be absorbent or non-absorbent. In some implementations, the flexible layers are of material suitable to prevent entry of fluids into the interior cavity of the pouch 202 (e.g., due to a water-proof or water-resistant coating). Thus, the first and/or second flexible layers 208 and 210 may be soft, pliable, and resistant to ripping or tearing.

In one particular example, the first flexible layer 208 includes a first layer of TPU and a first layer of nylon fabric. The second flexible layer 210 includes a second layer of TPU and a second layer of nylon fabric. For example, the first and second layers of TPU may respectively be located interior relative to the first and second layers of nylon fabric. In other words, the first and second layers of TPU may contact each other and may form an interior surface of the interior cavity of the pouch 202 while the first and second layers of nylon fabric are respectively carried by respective exterior surfaces of the first and second layers of TPU that are opposite to the interior cavity. Such may advantageously allow the first and second layers of TPU to more completely melt together or otherwise physically couple to each other when the RF weld 204 is generated. However, in other implementations, the first and second layers of nylon fabric may be located interior relative to the first and second layers of TPU or may be embedded within the first and second layers of TPU.

Figure 2B:
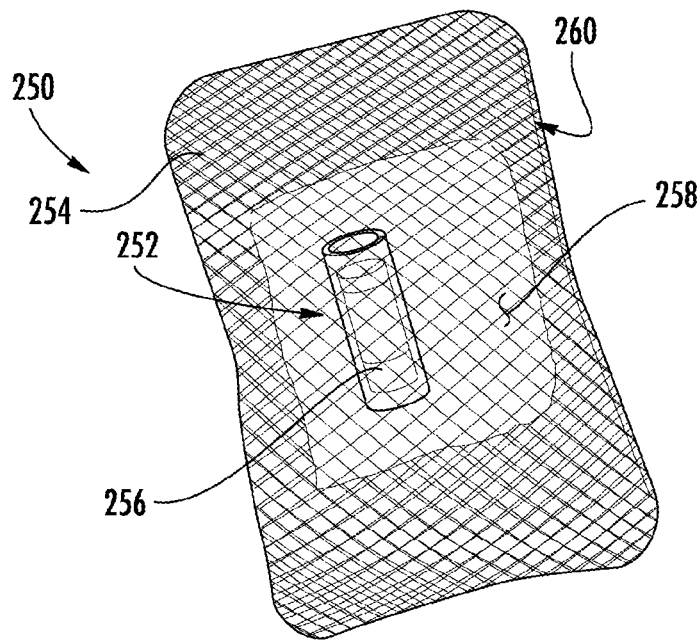
FIG. 2B is a front view of another pouch that includes a presence transponder, according to one illustrated embodiment.

FIG. 2B is another front view 250 of a pouch 252 that includes a presence transponder 256, according to one illustrated embodiment. In particular, pouch 252 includes a first flexible layer 258 physically coupled to a second flexible layer 260 by an RF weld 254. The presence transponder 256 is received and freely movable within an interior cavity formed between the first and second flexible layers 258 and 260. In particular, the RF weld 254 extends around a perimeter of the interior cavity and seals the presence transponder 256 within the interior cavity of the pouch 252. The pouch 252 is physically coupleable to an object 106 such as a piece of absorbent material.

Figure 3:
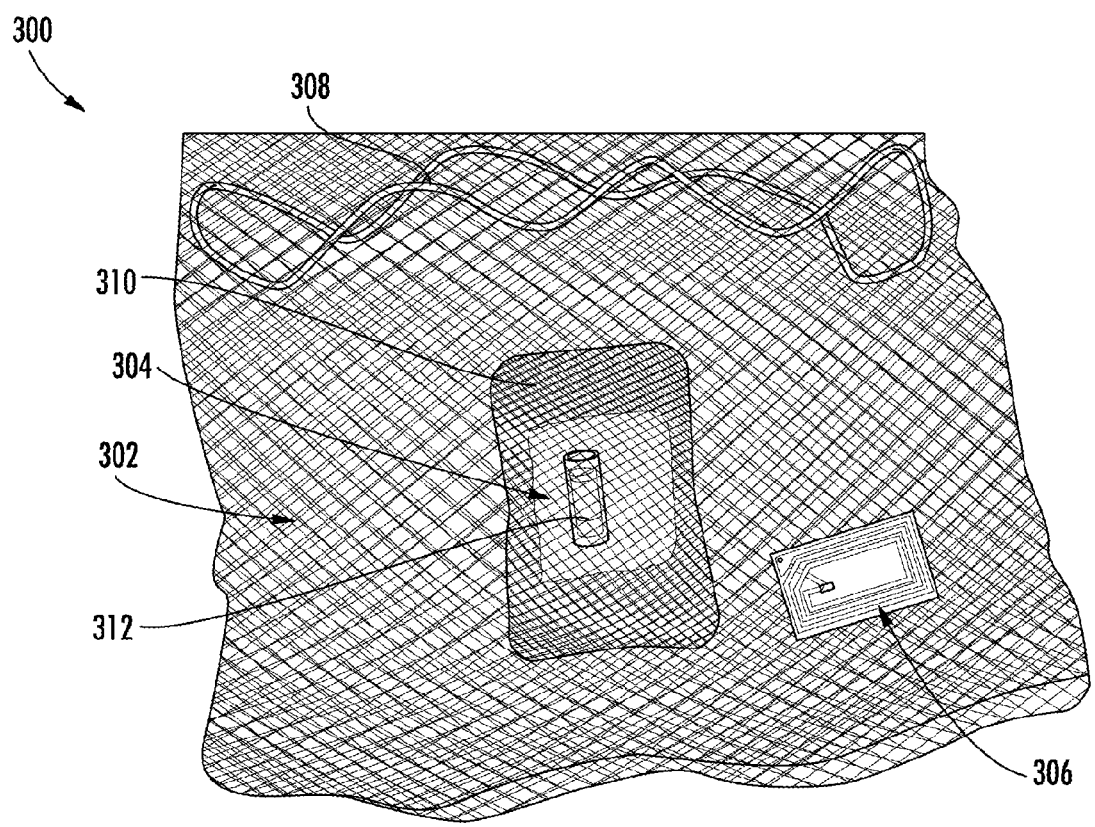
FIG. 3 is a front view of a piece of absorbent material with a wirelessly detectable object physically coupled thereto, according to one illustrated embodiment.

FIG. 3 is a front view 300 of a piece of absorbent material 302 with a wirelessly detectable object physically coupled thereto, according to one illustrated embodiment. In particular, an RFID transponder 306 and a presence transponder 312 are physically associated with the piece of absorbent material 302.

More precisely, a pouch 304 is physically coupled to the piece of absorbent material 302. The pouch 304 includes a first flexible layer physically coupled to a second flexible layer to form an interior cavity therebetween. The flexible layers may the same as or similar to layers 208 and 210 discussed with reference to FIG. 2A.

A presence transponder 312 is retained and freely movable within the interior cavity of the pouch 304. An RF weld 310 physically couples the first flexible layer to the second flexible layer. In some implementations, the RF weld 310 further physically couples the pouch 304 to the piece of absorbent material 302. In other implementations, an additional RF weld or other securing means physically couples the pouch 304 to the piece of absorbent material.

As shown in FIG. 3, the RFID transponder 306 is physically coupled to the piece of absorbent material 302 separately from the pouch 304. Adhesives, stitching, clamping, fasteners, heat sealing, RF welding, or other securing means physically couple the RFID transponder 306 the piece of absorbent material 302. In some implementations, a radiopaque thread or object 308 is woven into or otherwise physically coupled to the piece of absorbent material 302, as well.

Furthermore, although FIG. 3 depicts pouch 304 and RFID transponder 306 as physically coupled to and visible upon an external surface of the object piece of absorbent material 302, in some implementations, the piece of absorbent material 306 is be folded or otherwise manipulated such that the pouch 304 and RFID transponder 306 are internally carried between layers of the piece of absorbent material 302.

Figure 4:
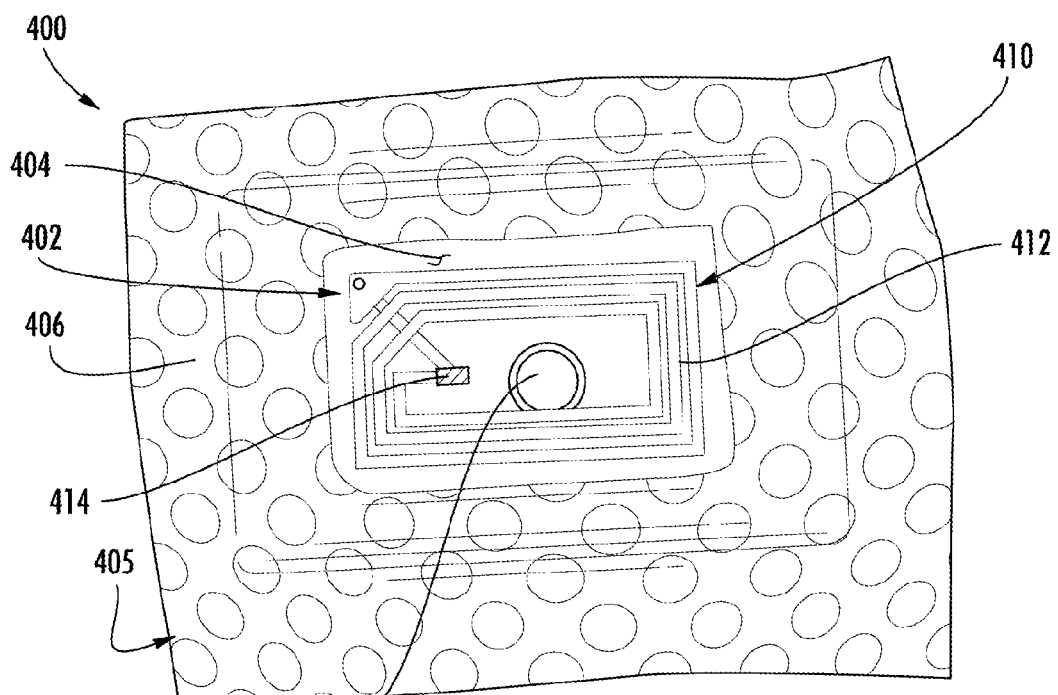
FIG. 4 is a front view of a pouch that includes a presence transponder freely movable within an interior cavity and an RFID transponder, according to one illustrated embodiment.

FIG. 4 is a front view 400 of a pouch 402 that includes a presence transponder 408 freely movable within an interior cavity and an RFID transponder 410 with an antenna trace 412, according to one illustrated embodiment.

The pouch 402 includes a first flexible layer 404 physically coupled to a second flexible layer 405 to form an interior cavity therebetween. The flexible layers 404 and 405 may the same as or similar to layers 208 and 210 discussed with reference to FIG. 2A.

The presence transponder 408 is retained and freely movable within the interior cavity of the pouch 402. In particular, an RF weld 406 physically couples the first flexible layer 404 to the second flexible layer 405 and seals the presence transponder 408 within the interior cavity.

The RFID transponder 410 includes an antenna trace 412 electrically coupled to a chip 414. An integrated circuit that stores identification information can form all or a portion of the chip 414.

All or a portion of the RFID transponder 410 can be embedded in and/or adhered to the first flexible layer 404. For example, in some implementations, the chip 414 is adhered to the first flexible layer 404 (e.g., adhered to a surface of the first layer 404 that faces the interior cavity) while the antenna trace 412 is embedded within the first flexible layer 404. In other implementations, the antenna trace 412 is printed or traced onto the first flexible layer 404 (e.g., onto an interior surface that faces the interior cavity). In yet other implementations, all or a portion of the RFID transponder 410 is embedded in and/or adhered to the second flexible layer 405.

In some implementations, at least a portion of the first flexible layer 404 and/or the second flexible layer 405 is a material that is absorbent but remains electrically insulative, thereby contributing to an absorbency of an attached piece of absorbent material without interfering with an ability of the antenna trace 412 to transmit a signal.

As the presence transponder 408 is freely movable within the interior cavity of the pouch 402 and the RFID transponder 410 is embedded in and/or adhered to the first flexible layer 404, the presence transponder 408 is independently movable with respect to the RFID transponder 410. Furthermore, as shown in FIG. 4, in some implementations, care is taken to prevent the RF weld 406 from welding over and potentially damaging the antenna trace 412.

Figure 5A:
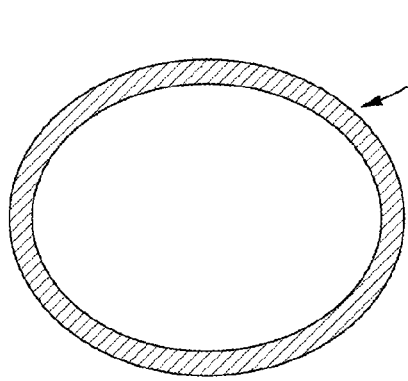
FIG. 5A is a top view of a pouch, according to one illustrated embodiment.
Figure 5B:
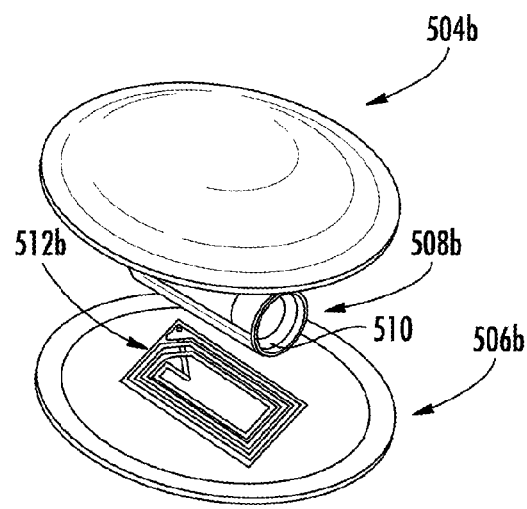
FIG. 5B is an exploded isometric view of a pouch that includes a presence transponder freely movable within an interior cavity and an RFID transponder adhered to a second layer of the pouch, according to one illustrated embodiment.

FIG. 5A is a top view of a pouch 502, according to one illustrated embodiment. FIG. 5B is an exploded isometric view of the pouch 502 that includes a presence transponder 508b freely movable within an interior cavity formed between a first flexible layer 504b and a substrate 506b of the pouch, according to one illustrated embodiment. An RFID transponder 512b is adhered to the substrate 506b. An encapsulant 510 encapsulates the presence transponder 508b. The substrate 506b can be a second flexible layer, a surgical object such as a piece of absorbent material, or other substrates. In particular, the first flexible layer 504b and the substrate 506b may the same as or similar to layers 208 and 210 discussed with reference to FIG. 2A. In some implementations, an RF weld physically couples the first flexible layer 504b to the substrate 506b.

Figure 5C:
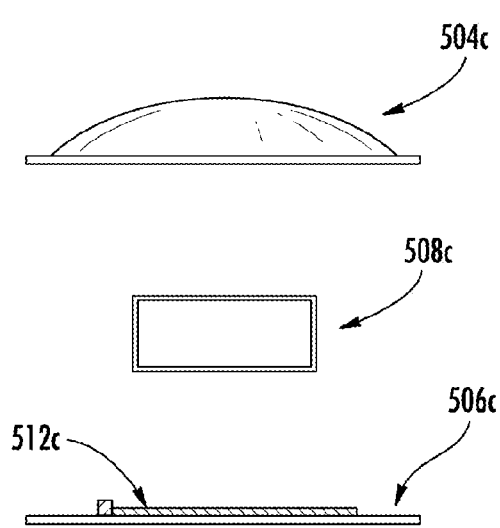
FIG. 5C is first and second exploded side views of a pouch that includes a presence transponder freely movable within an interior cavity and an RFID transponder adhered to a second layer of the pouch, according to one illustrated embodiment.

FIG. 5C is first and second exploded side views of the pouch 502 that includes the presence transponder 508c freely movable within the interior cavity formed between the first flexible layer 504c and the substrate 506c of the pouch, according to one illustrated embodiment. The RFID transponder 512c is adhered to the substrate 506c of the pouch 502. For example, in some implementations, some or all of the RFID transponder 512c (e.g., a chip portion) is adhered to the substrate 506c using adhesives or other securing means. In some implementations, some or all of the RFID transponder 512c (e.g., an antenna portion) is printed onto or traced upon the substrate 506c.

Figure 6A:
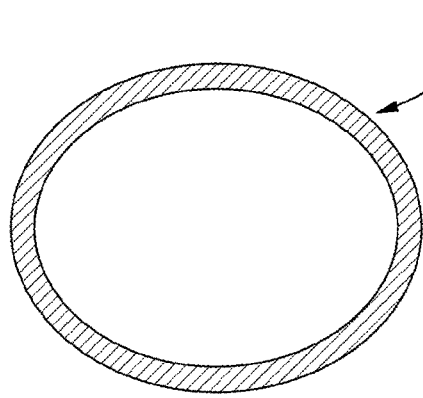
FIG. 6A is a top view of a pouch, according to one illustrated embodiment.
Figure 6B:
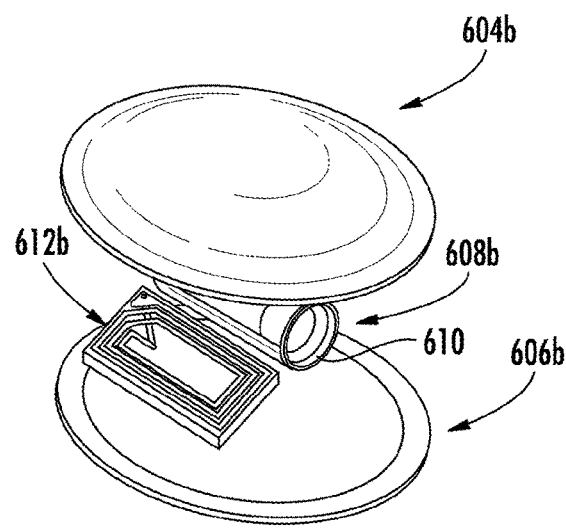
FIG. 6B is an exploded isometric view of a pouch that includes a presence transponder and an RFID transponder freely movable within an interior cavity, according to one illustrated embodiment.

FIG. 6A is a top view of a pouch 602, according to one illustrated embodiment. FIG. 6B is an exploded isometric view of the pouch 602 that includes a presence transponder 608b and an RFID transponder 612b freely movable within an interior cavity formed between a first flexible layer 604b and a substrate 606b of the pouch, according to one illustrated embodiment. An encapsulant 610 encapsulates the presence transponder 608b. The substrate 606b can be a second flexible layer, a surgical object such as a piece of absorbent material, or other substrates. In particular, the first flexible layer 604b and the substrate 606b may the same as or similar to layers 208 and 210 discussed with reference to FIG. 2A. In some implementations, an RF weld physically couples the first flexible layer 604b to the substrate 606b.

Figure 6C:
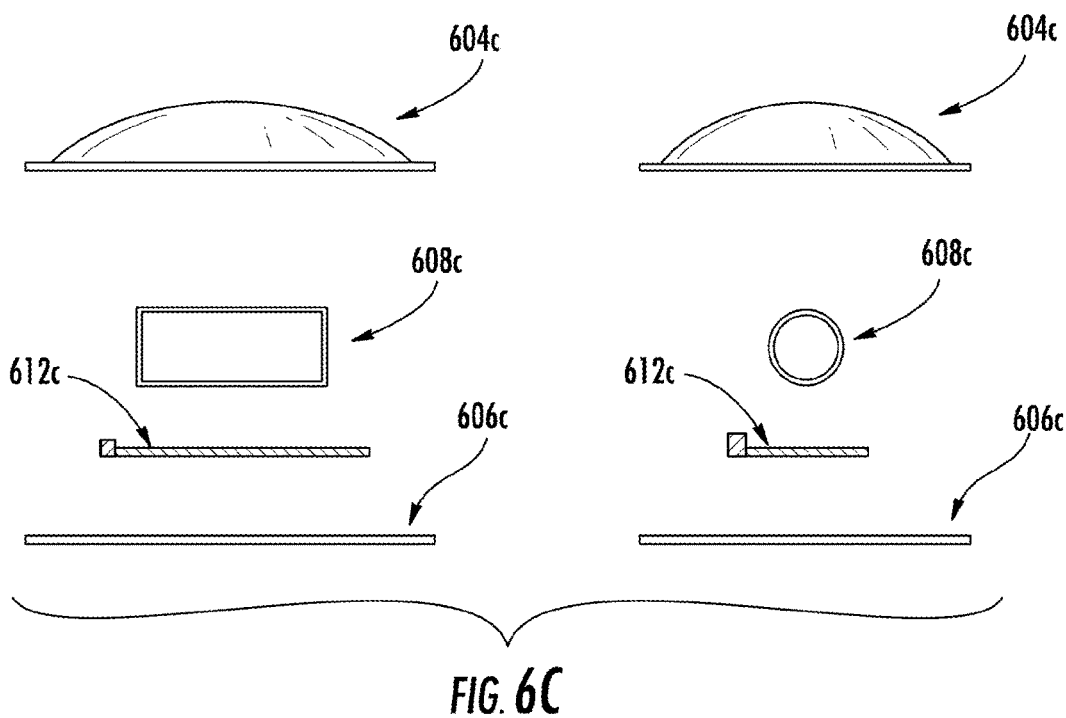
FIG. 6C is first and second exploded side views of a pouch that includes a presence transponder and an RFID transponder freely movable within an interior cavity, according to one illustrated embodiment.

FIG. 6C is first and second exploded side views of the pouch 602 that includes the presence transponder 608c and the RFID transponder 612c freely movable within the interior cavity formed between the first flexible layer 604c and the substrate 606c of the pouch, according to one illustrated embodiment.

Figure 7:
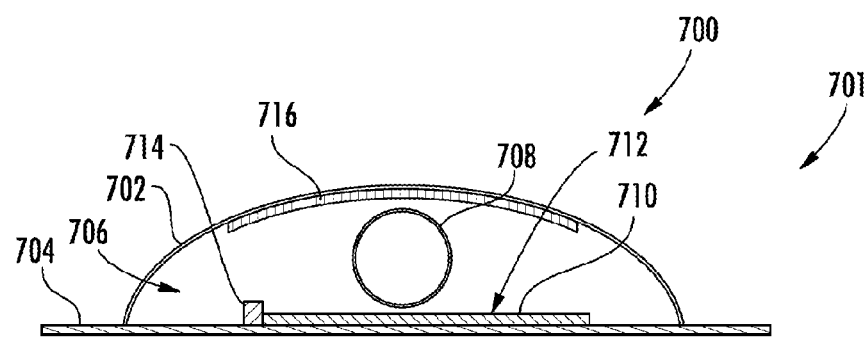
FIG. 7 is a cross-sectional diagram of a wirelessly detectable object that includes a directional antenna formed on or within a pouch, according to one illustrated embodiment.

FIG. 7 is a cross-sectional diagram of a wirelessly detectable object 700 that includes a directional antenna formed on or within a pouch 701, according to one illustrated embodiment. In particular, the pouch 701 includes a first flexible layer 702 physically coupled to a substrate 704 to form an interior cavity 706 therebetween. A presence transponder 708 is received and freely movable within the interior cavity 706. The substrate 704 can be a second flexible layer, a surgical object such as a piece of absorbent material, or other substrates. In particular, the first flexible layer 702 and the substrate 704 may the same as or similar to layers 208 and 210 discussed with reference to FIG. 2A.

The wirelessly detectable object further includes an RFID transponder 710 that includes at least one active antenna element 712 and an integrated circuit 714. For example, the integrated circuit 714 can actively drive or energize the active antenna element 712 of the RFID transponder 710 to transmit a signal.

According to an aspect of the present disclosure, the wirelessly detectable object 700 further includes at least one passive antenna element 716 that, together with the active antenna element 712, operates as a directional antenna. For example, the passive antenna element 716 and the active antenna element 712 may together operate as a Yagi antenna.

As shown in FIG. 7, the passive antenna element 716 can be a separate structure from the active antenna element 712 of the RFID transponder 710. However, in other implementations, the passive antenna element 716 and the active antenna element 712 may be included within a single integral structure. In some implementations, two or more passive antenna elements 716 act as a reflector element and a director element, respectively.

As shown in FIG. 7, the passive antenna element 716 is adhered to or traced upon an interior surface of the first flexible layer 702 that faces the interior cavity 706. However, in other implementations, the passive antenna element 716 may be at least partially embedded in the first flexible layer 702 or adhered to or traced upon an exterior surface of the first flexible layer 702. The active antenna element 712 is adhered to or traced upon an interior surface of the substrate 704 that faces the interior cavity 706. However, in other implementations, the active antenna element 712 may be at least partially embedded within the substrate 704 or adhered to or traced upon an exterior surface of the substrate 704.

In yet further implementations, the respective positions of the active antenna element 712 and the passive antenna element 716 may be opposite to those depicted in FIG. 7. That is, the passive antenna element 716 may be adhered to or embedded within the substrate 704 while the active antenna element 712 is adhered to or embedded within the first flexible layer 702.

Figure 8:
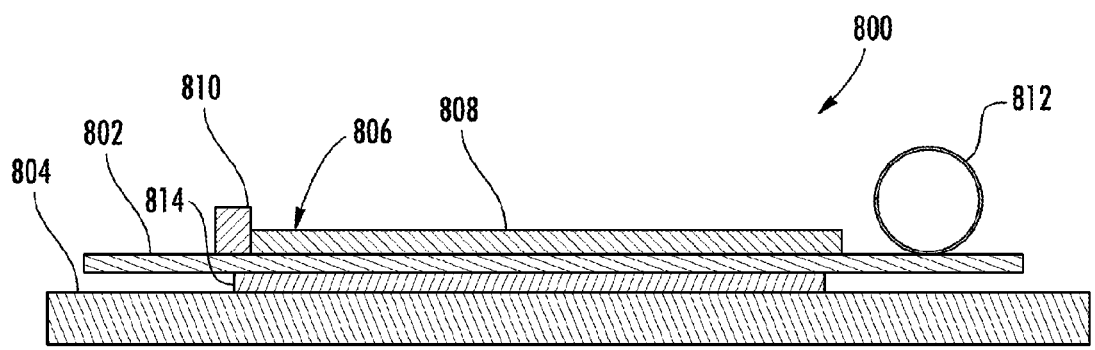
FIG. 8 is a cross-sectional diagram of a wirelessly detectable object that includes a directional antenna carried at least in part by a first substrate, according to one illustrated embodiment.

FIG. 8 is a cross-sectional diagram of a wirelessly detectable object 800 that includes a directional antenna carried at least in part by a first substrate 802, according to one illustrated embodiment. The wirelessly detectable object 800 further includes an RFID transponder 806 and a presence transponder 812 physically coupled to the first substrate 802. The wirelessly detectable object 800 is physically coupled to a piece of absorbent material 804.

The first substrate 802 may be a first flexible layer. For example, the first substrate 802 may be the same as or similar to layers 208 and 210 discussed with reference to FIG. 2A.

The RFID transponder 806 includes an active antenna element 808 and an integrated circuit 810. For example, the integrated circuit 810 may selectively actively energize or otherwise cause the active antenna element 808 to radiate to transmit a signal. The wirelessly detectable object 800 further includes at least one passive antenna element 814 that, together with the active antenna element 808, operates as a directional antenna. For example, the passive antenna element 814 and the active antenna element 808 may together operate as a Yagi antenna.

As shown in FIG. 8, the passive antenna element 814 is positioned between the first substrate 802 and the piece of absorbent material 804. For example, the passive antenna element 814 can be adhered to, traced onto, or otherwise carried by one or both of the first substrate 802 and/or the piece of absorbent material 804. However, in other implementations, at least a portion of the passive antenna element 814 is embedded within or forms a portion of the first substrate 802 or the piece of absorbent material 804.

In yet further implementations, the respective positions of the active antenna element 808 and the passive antenna element 814 may be opposite to those depicted in FIG. 8. That is, the passive antenna element 814 may be adhered to or carried by a surface of the first substrate 802 that is opposite the piece of absorbent material 804 while the active antenna element 808 is positioned between the first substrate 802 and the piece of absorbent material 804.

While FIG. 8 depicts first substrate 802 as not contacting the piece of absorbent material 804, in some implementations, the first substrate 802 is physically coupled to (e.g., by an RF weld) the piece of absorbent material 804. Further, in some implementations, the wirelessly detectable object 800 does not include the presence transponder 812.

Figure 9:
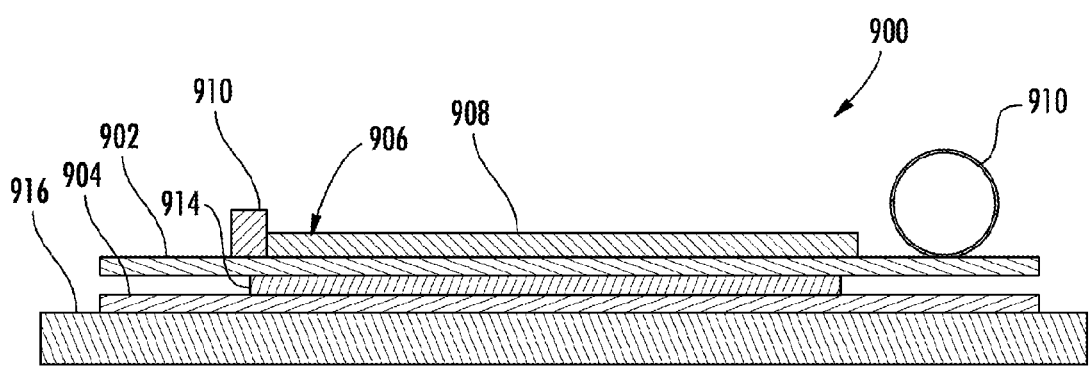
FIG. 9 is a cross-sectional diagram of a wirelessly detectable object that includes a directional antenna carried at least in part by each of a first and second substrate, according to one illustrated embodiment.

FIG. 9 is a cross-sectional diagram of a wirelessly detectable object 900 that includes a directional antenna carried at least in part by a first substrate 902, according to one illustrated embodiment. The wirelessly detectable object 900 is physically coupled to a piece of absorbent material 916.

The wirelessly detectable object 900 includes an RFID transponder 906 and a presence transponder 910 physically coupled to the first substrate 902. The wirelessly detectable object 900 further includes a second substrate 904. The first substrate 902 and/or the second substrate 904 may be flexible layers. For example, the first substrate 902 and/or the second substrate 904 may be the same as or similar to layers 208 and 210 discussed with reference to FIG. 2A.

The RFID transponder 906 includes an active antenna element 908 and an integrated circuit 910. For example, the integrated circuit 910 may selectively actively energize or otherwise cause the active antenna element 908 to radiate to transmit a signal. The wirelessly detectable object 900 further includes at least one passive antenna element 914 that, together with the active antenna element 908, operates as a directional antenna. For example, the passive antenna element 914 and the active antenna element 908 may together operate as a Yagi antenna.

As shown in FIG. 9, the passive antenna element 914 is positioned between the first substrate 902 and the second substrate 904. For example, the passive antenna element 914 can be adhered to, traced onto, or otherwise carried by one or both of the first substrate 902 and/or the second substrate 904. However, in other implementations, at least a portion of the passive antenna element 914 is embedded within or forms a portion of the first substrate 902 or the second substrate 904.

In yet further implementations, the respective positions of the active antenna element 908 and the passive antenna element 914 may be opposite to those depicted in FIG. 9. That is, the passive antenna element 914 may be adhered to or carried by a surface of the first substrate 902 that is opposite the second substrate 904 while the active antenna element 908 is positioned between the first substrate 902 and the second substrate 904. Further, in some implementations, one or more RF welds or other securing means physically couple one or both of the first and second substrates 902 and 904 to the piece of absorbent material 916.

Furthermore, while FIG. 9 depicts first substrate 802 as not contacting the second substrate 904, in some implementations, the first substrate 902 is physically coupled to (e.g., by an RF weld) the second substrate 904. Likewise, an RF weld may physically couple the second substrate 904 to the piece of absorbent material. Further, in some implementations, the wirelessly detectable object 900 does not include the presence transponder 910.

Figure 10:
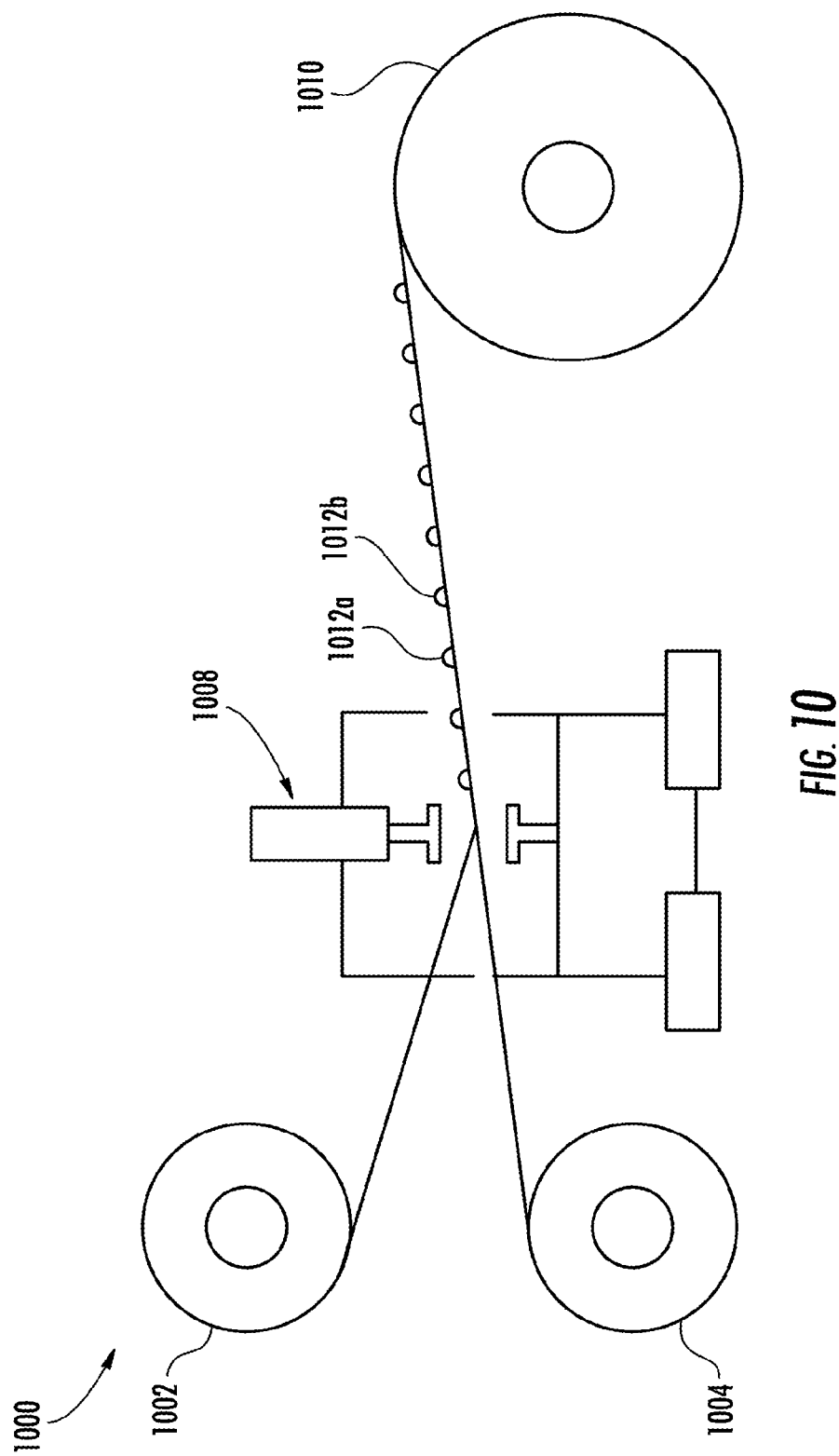
FIG. 10 is a schematic diagram of a method for manufacturing wirelessly detectable objects using RF welding, according to one illustrated embodiment.

FIG. 10 is a schematic diagram 1000 of a method for manufacturing wirelessly detectable objects using RF welding, according to one illustrated embodiment. In particular, the method may include providing a first flexible layer 1002 and a second flexible layer 1004. For example, either or both of the first flexible layer 1002 and the second flexible layer 1004 may be the same as or similar to layers 208 and 210 discussed with reference to FIG. 2A. In some implementations, as shown in FIG. 10, the first and/or second flexible layers 1002 and 1004 may be provided as rolls or sheets of flexible layers.

The method may further include RF welding the first flexible layer 1002 to the second flexible layer 1004 to form a plurality of pouches (e.g., pouches 1012a and 1012b).

Each of the plurality of pouches can be formed by a set of RF welds. For example, an RF welding machine 1008 can be used to create a plurality of RF welds that physically couple the first flexible layer 1002 to the second flexible layer 1004 and create the plurality of pouches 1012a and 1012b. Each set of RF welds can take the form of a hollowed rectangle, circle, oval, or other shape to form an interior cavity within a perimeter of the hollowed area. One or more transponders can be sealed within the interior cavity of each pouch 1012.

Thus, through automatic or manual operation of the RF welding machine 1008 to generate the plurality of RF welds, the first and second flexible layers 1002 and 1004 are transformed into a sheet or roll of pouches 1010, with each pouch 1012 retaining one or more transponders. As such, rather than being discretely made from the assembly of individual components, the pouches 1012 may come as a roll of pouches 1010 each containing one or more respective transponders. Having the pouches 1012 come in a roll 1010 enhances the efficiency in the manufacturing process, as all that remains to be done is cutting or separating the pouches 1012 from the roll 1010 and attaching each of the pouches 1012 to a respective surgical object.

Figure 11:
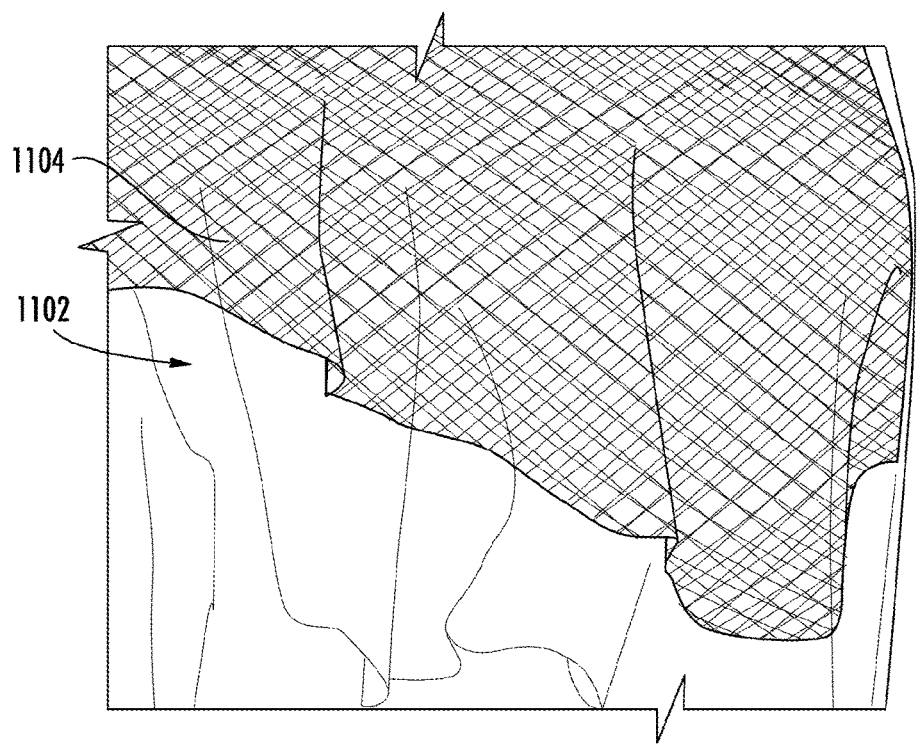
FIG. 11 shows flexible layers usable to manufacture a plurality of pouches, according to one illustrated embodiment.

FIG. 11 shows flexible layers usable to manufacture a plurality of pouches, according to one illustrated embodiment. In particular, FIG. 11 shows a first flexible layer 1102 of thermoplastic polyurethane and a second flexible layer 1104 of nylon. The above noted materials are provided as examples only. In particular, the flexible layers 1102 and 1104 may be the same as or similar to layers 208 and 210 discussed with reference to FIG. 2A.

Figure 12:
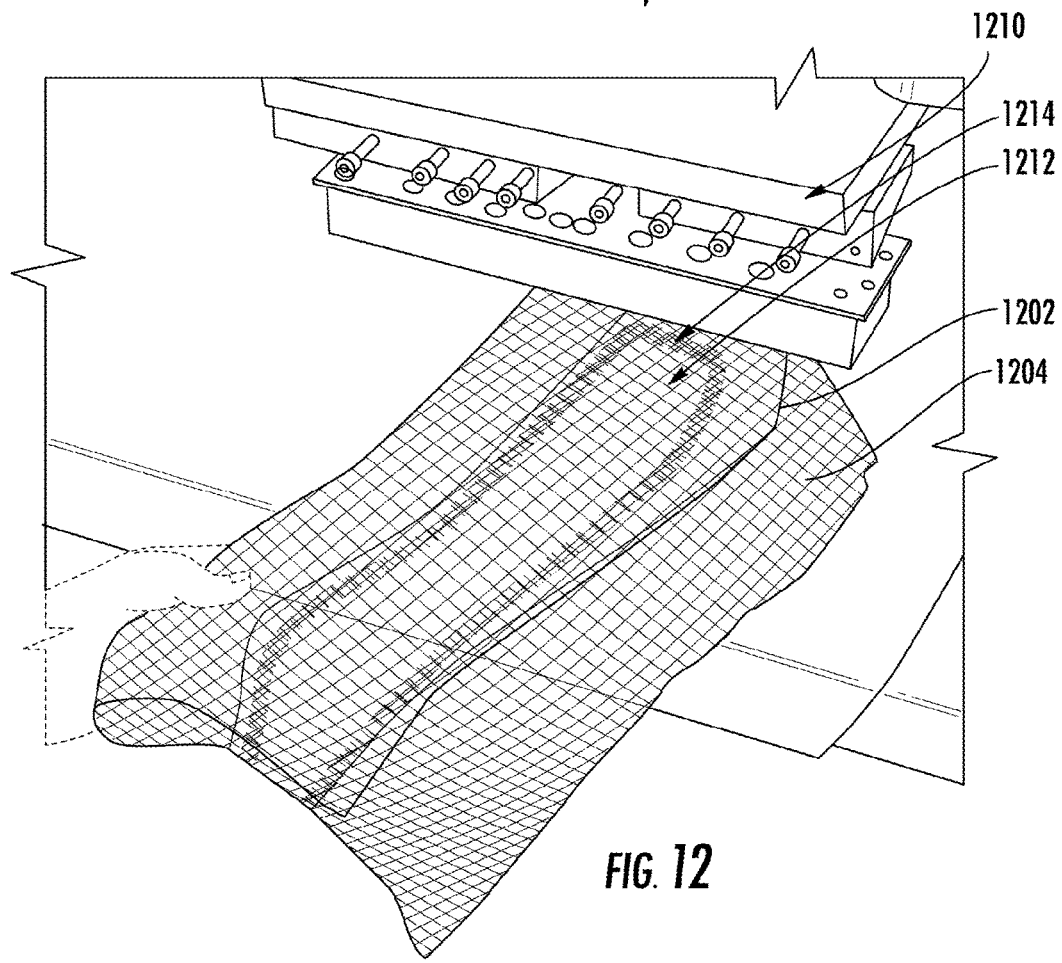
FIG. 12 shows manufacture of a plurality of pouches using an RF welding technique, according to one illustrated embodiment.

FIG. 12 shows manufacture of a plurality of pouches using an RF welding technique, according to one illustrated embodiment. In particular, FIG. 12 shows the first flexible layer 1102 of thermoplastic polyurethane and the second flexible layer 1104 of nylon. An RF welding machine 1210 is used to generate a plurality of RF welds to physically couple layer 1102 to layer 1104 and form a plurality of pouches. As an example, an RF weld 1214 forms at least a portion of a perimeter of an interior cavity of an unfinished pouch 1212. One or more transponders (not shown) may be positioned between layers 1102 and 1104 and then sealed within the pouch 1212 by an additional RF weld.

As one example method of manufacture, the pouches may be made by RF welding the first layer 1102 to the second layer 1104 where a series of cavities for receiving one or more corresponding transponders are made by providing bulges in the first layer 1102 and/or the second layer 1104. The bulges may be formed by bunching or stretching the material of the first layer 1102 and/or the second layer 1104.

Figure 13:
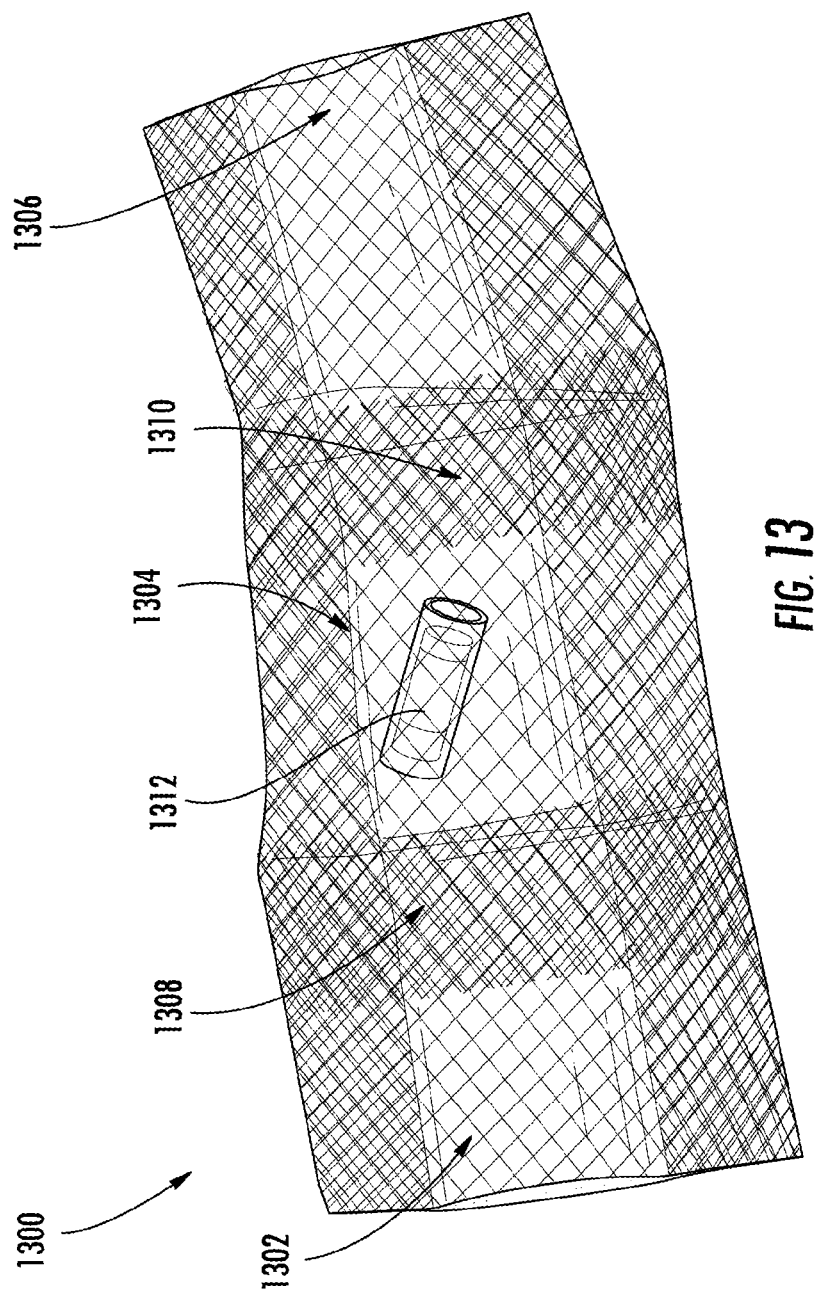
FIG. 13 is a front view of a plurality of pouches manufactured using an RF welding technique, according to one illustrated embodiment.

FIG. 13 is a front view 1300 of a plurality of pouches 1302, 1304, and 1306 manufactured using the RF welding technique illustrated in FIGS. 10 and 12, according to one illustrated embodiment. In particular, a plurality of RF welds form each of pouches 1302, 1304, and 1306. For example, RF welds 1308 and 1310 form at least a portion of a perimeter of an interior cavity of pouch 1304. A presence transponder 1312 is received and freely movable within the interior cavity of pouch 1304. Pouches 1302 and 1306 are bisected for the purposes of illustration. The pouches 1302, 1304, and 1306 may be physically separated (e.g., cut apart) and then respectively physically coupled to surgical objects to act as wirelessly detectable objects.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other absorbent materials, other types of transponders, and other interrogation and detection systems. For instance, the transponder device may be used to mark objects anytime detection of the presence of marked objects is desirable in a confined area, not just during surgery. For example, it may be used to make sure marked objects are not left inside a machine (e.g., vehicle, copy machine) after maintenance is performed. In at least some embodiments, the transponder housing may be utilized to mark objects to determine the removal of a marked object from a confined area, such as a cover-all garment from a clean room of a semiconductor fabrication plant. In such an embodiment, an interrogation device, for example, may be placed proximate to a door of the confined area.

In addition, a transponder housing or cover may be manufactured and distributed for tagging objects without a transponder currently attached. Advantageously, the housing can then be used to place a transponder compatible with a particular detection and interrogation system at a subsequent time, including by the end-user.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Pat. No. 8,358,212; U.S. Pat. No. 8,710,957; U.S. Pat. No. 8,726,911; U.S. Patent Application Publication No. 2010/0108079; U.S. Provisional Patent Application Ser. No. 60/811,376 filed Jun. 6, 2006; U.S. Provisional Patent Application Ser. No. 60/892,208, filed Feb. 28, 2007; U.S. Provisional Patent Application Ser. No. 61/109,142 filed Oct. 28, 2008 and U.S. Provisional Patent Application Ser. No. 62/106,052 filed Jan. 21, 2015 are incorporated herein by reference, in their entirety. Aspects of the embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

What is claimed is:

1. A wirelessly detectable object to use in medical procedures, comprising:
    a radio frequency identification (RFID) transponder that wirelessly receives a first interrogation signal and wirelessly returns a first response signal that contains identification information associated with the wirelessly detectable object;
    a presence transponder that wirelessly receives a second interrogation signal and wirelessly returns a second response signal that does not contain identification information;
    a piece of absorbent material; and
    a pouch comprising at least a first flexible layer that forms an interior cavity, the presence transponder received and freely movable within the interior cavity, the presence transponder independently movable with respect to the RFID transponder, the pouch physically coupled to at least a portion of the piece of absorbent material.

2. The wirelessly detectable object of claim 1 wherein the presence transponder is not directly physically attached to the RFID transponder.

3. The wirelessly detectable object of claim 1 wherein the RFID transponder is received within the interior cavity.

4. The wirelessly detectable object of claim 1 wherein the RFID transponder is received and freely movable within the interior cavity.

5. The wirelessly detectable object of claim 1 wherein the RFID transponder forms at least a portion of the first flexible layer, is embedded within the first flexible layer, or is adhered to the first flexible layer.

6. The wirelessly detectable object of claim 1 wherein the RFID transponder comprises an RFID chip and an antenna trace.

7. The wirelessly detectable object of claim 6 wherein either or both of the RFID chip and the antenna trace are embedded within the first flexible layer.

8. The wirelessly detectable object of claim 6 wherein the antenna trace of the RFID transponder comprises an active antenna element, the wirelessly detectable object further comprises a passive antenna element, and the active antenna element and the passive antenna element together form a directional antenna.

9. The wirelessly detectable object of claim 8 wherein the passive antenna element is embedded in the first flexible layer.

10. The wirelessly detectable object of claim 9 wherein the first flexible layer is physically coupled to the piece of absorbent material to form the interior cavity therebetween and at least the active antenna element of the RFID transponder is received within the interior cavity and adhered to the piece of absorbent material.

11. The wirelessly detectable object of claim 1 wherein the pouch further comprises a second flexible layer physically coupled to the first flexible layer to form the interior cavity therebetween, the second flexible layer different than the piece of absorbent material.

12. The wirelessly detectable object of claim 11 wherein the RFID transponder forms at least a portion of the second flexible layer, is embedded within the second flexible layer, or is adhered to the second flexible layer.

13. The wirelessly detectable object of claim 10, further comprising:
a passive antenna element embedded in or adhered to the first flexible layer, the passive antenna element and the RFID transponder together forming a directional antenna.

14. The wirelessly detectable object of claim 11 wherein the pouch further comprises a radio frequency (RF) weld that extends around a perimeter of the interior cavity, physically couples the first flexible layer to the second flexible layer, and seals the presence transponder within the interior cavity.

15. The wirelessly detectable object of claim 14 wherein the RF weld comprises a first RF weld and wherein the first RF weld or a second RF weld further physically couples the pouch to the piece of absorbent material.

16. The wirelessly detectable object of claim 11 wherein one or both of the first flexible layer and second flexible layer are a fabric laminate.

17. The wirelessly detectable object of claim 1 wherein the pouch further comprises a radio frequency (RF) weld that extends around a perimeter of the interior cavity, physically couples the first flexible layer to the piece of absorbent material, and seals the presence transponder within the interior cavity.

18. The wirelessly detectable object of claim 1 wherein the first flexible layer is formed of a fabric laminate.

19. The wirelessly detectable object of claim 16 wherein the fabric laminate comprises thermoplastic polyurethane and nylon fabric or polyvinyl chloride (PVC) impregnated fabric.

20. A wirelessly detectable object to use in medical procedures, comprising:
a piece of absorbent material;
a first substrate physically coupled to the piece of absorbent material;
a radio frequency identification (RFID) transponder to wirelessly receive a first interrogation signal and wirelessly return a first response signal that contains identification information associated with the wirelessly detectable object, the RFID transponder comprising an active antenna element; and
a passive antenna element;
wherein the passive antenna element and the active antenna element together operate as a directional antenna and the first substrate carries at least one of the active antenna element and the passive antenna element.

21. The wirelessly detectable object of claim 20 wherein the first substrate comprises a layer of fabric laminate.

22. The wirelessly detectable object of claim 21 wherein the fabric laminate is physically coupled to the piece of absorbent material to form an interior cavity therebetween and the wirelessly detectable object further comprises a presence transponder received and freely movable within the interior cavity, the presence transponder to wirelessly return a second response signal that does not contain identification information.

23. The wirelessly detectable object of claim 22 wherein the RFID transponder is embedded in or adhered to the layer of fabric laminate or is received within the interior cavity and adhered to the piece of absorbent material.

24. The wirelessly detectable object of claim 21 wherein the passive antenna element is located between the piece of absorbent material and the layer of fabric laminate and the active antenna element is embedded in, adhered to, or forms a portion of the layer of fabric laminate.

25. The wirelessly detectable object of claim 21 wherein the active antenna element is located between the piece of absorbent material and the layer of fabric laminate and the passive antenna element is embedded in, adhered to, or forms a portion of the layer of fabric laminate.

26. The wirelessly detectable object of claim 24 wherein the layer of fabric laminate is carried at least in part by one or more of the passive antenna element and the active antenna element.

27. The wirelessly detectable object of claim 24, further comprising:
a second layer of fabric laminate located between the passive antenna element and the piece of absorbent material.

28. The wirelessly detectable object of claim 20, further comprising:
a presence transponder physically coupled to the piece of absorbent material, the presence transponder to wirelessly return a second response signal that does not contain identification information.

29. The wirelessly detectable object of claim 20 wherein the directional antenna comprises a Yagi antenna.

30. The wirelessly detectable object of claim 20 where one or both of the active antenna element and the passive antenna element comprise conductive traces embedded within or carried on the first substrate.

31. A method to account for surgical objects used in medical procedures, the method comprising:
providing a plurality of surgical objects that have a plurality of wirelessly detectable objects respectively physically coupled thereto, each wirelessly detectable object comprising a radio frequency identification (RFID) transponder and a presence transponder;
interrogating the RFID transponder of each surgical object introduced into a surgical field;
receiving, from the interrogated RFID transponder of each surgical object introduced into the surgical field, a first response signal that contains identification information stored by such RFID transponder;
generating a first manifest of surgical objects introduced into the surgical field based at least in part on the identification information included in each first response signal;
prior to completion of a medical procedure, scanning the surgical field to interrogate any presence transponders that remain within the surgical field;
determining whether any surgical objects remain within the surgical field based at least in part on whether one or more second response signals are respectively received from one or more presence transponders responsive to the scanning, wherein the one or more second response signals do not contain identification information;

interrogating the RFID transponder of each surgical object removed from the surgical field;

receiving, from the interrogated RFID transponder of each surgical object removed from the surgical field, a third response signal that contains the identification information stored by such RFID transponder; and generating a second manifest of surgical objects removed from the surgical field based at least in part on the identification information included in each third response signal.

32. The method of claim 31 wherein receiving a first response signal comprises receiving the first response signal that is within a first frequency range, and determining whether any surgical objects remain within the surgical field comprises determining whether any surgical objects remain within the surgical field based at least in part on whether one or more second response signals are respectively received from one or more presence transponders responsive to the scanning, the one or more second response signals within a second frequency range that provides superior transmission through bodily tissue relative to the first frequency range.

33. The method of claim 31 wherein receiving a first response signal comprises receiving the first response signal at a first physical distance from each RFID transponder, and determining whether any surgical objects remain within the surgical field comprises determining whether any surgical objects remain within the surgical field based at least in part on whether one or more second response signals are respectively received at a second physical distance from one or more presence transponders responsive to the scanning, the second physical distance greater than the first physical distance.

34. The method of claim 31, further comprising:
comparing the first manifest to the second manifest to determine whether one or more surgical objects remain within the surgical field.

* * * * *